US006403311B1

(12) United States Patent
Chan

(10) Patent No.: US 6,403,311 B1
(45) Date of Patent: Jun. 11, 2002

(54) METHODS OF ANALYZING POLYMERS USING ORDERED LABEL STRATEGIES

(75) Inventor: Eugene Y. Chan, Boston, MA (US)

(73) Assignee: US Genomics, Woburn, MA (US)

( * ) Notice: Subject to any disclaimer, the term of this patent is extended or adjusted under 35 U.S.C. 154(b) by 0 days.

(21) Appl. No.: 09/374,415

(22) Filed: Aug. 13, 1999

Related U.S. Application Data

(63) Continuation-in-part of application No. 09/134,411, filed as application No. PCT/US98/03024 on Feb. 11, 1998.
(60) Provisional application No. 60/096,666, filed on Aug. 13, 1998, provisional application No. 60/120,662, filed on Aug. 13, 1998, provisional application No. 60/096,687, filed on May 5, 1997, and provisional application No. 60/037,921, filed on Feb. 12, 1997.

(51) Int. Cl.$^7$ ................................................. C12Q 1/68
(52) U.S. Cl. ............................... 435/6; 435/375; 435/5; 204/182.8; 935/77; 935/78; 436/94; 548/416; 549/382; 546/33
(58) Field of Search .............................. 435/6, 375, 5; 204/182.8; 935/77, 78; 436/94; 548/416; 549/382; 546/33

(56) References Cited

U.S. PATENT DOCUMENTS

| | | | |
|---|---|---|---|
| 4,764,460 A | * 8/1988 | Furuichi et al. ............... 435/6 |
| 4,793,705 A | 12/1988 | Shera ......................... 356/318 |
| 5,079,169 A | 1/1992 | Chu et al. .................... 436/172 |
| 5,091,652 A | 2/1992 | Mathies et al. ......... 250/458.1 B |
| 5,171,534 A | 12/1992 | Smith et al. ............. 422/82.05 |
| 5,274,240 A | 12/1993 | Mathies et al. .......... 250/458.1 |
| 5,356,776 A | * 10/1994 | Kambara et al. .............. 435/6 |
| 5,424,841 A | 6/1995 | Van Gelder et al. ........ 356/417 |
| 5,436,130 A | 7/1995 | Mathies et al. ............... 435/6 |
| 5,459,325 A | 10/1995 | Hueton et al. ............ 250/458.1 |
| 5,470,707 A | 11/1995 | Sasaki et al. .................. 435/6 |
| 5,492,806 A | * 2/1996 | Drmanac et al. .............. 435/5 |
| 5,538,848 A | 7/1996 | Livak et al. .................... 435/5 |
| 5,538,898 A | 7/1996 | Wickramasinghe et al. ... 436/94 |
| 5,635,728 A | 6/1997 | Cantu et al. ................ 250/584 |
| 5,654,419 A | 8/1997 | Mathies et al. ............. 536/25.4 |
| 5,674,743 A | 10/1997 | Ulmer ...................... 435/287.2 |
| 5,720,928 A | 2/1998 | Schwartz ..................... 422/186 |
| 5,723,332 A | 3/1998 | Chernajovsky .......... 435/320.1 |
| 5,789,167 A | * 8/1998 | Konrad ........................... 435/6 |
| 5,795,782 A | 8/1998 | Church et al. ................ 436/2 |
| 5,830,659 A | 11/1998 | Stewart .......................... 435/6 |
| 5,869,255 A | 2/1999 | Mathies et al. ................. 435/6 |
| 5,888,792 A | 3/1999 | Bandman et al. ............ 438/183 |
| 5,906,723 A | 5/1999 | Mathies et al. .............. 204/603 |
| 5,928,869 A | 7/1999 | Nadeau et al. ................. 435/6 |
| 5,932,442 A | 8/1999 | Lal et al. .................... 435/69.1 |
| 6,015,714 A | 1/2000 | Baldarelli et al. .............. 436/2 |
| 6,051,719 A | * 4/2000 | Benson et al. ................ 548/416 |
| 6,054,316 A | * 4/2000 | Baker et al. ................. 435/375 |

FOREIGN PATENT DOCUMENTS

| WO | WO 96/29593 | 9/1996 |
| WO | WO96/30508 A | 10/1996 |
| WO | PCT/US98/03024 | 10/1998 |

OTHER PUBLICATIONS

Akerman, B., et al. 1990. "Electrophoretic orientation of DNA detected by linear dichroism spectroscopy," J. Chem. Soc. D. Chem. Commun.: 422.
Aikens, R. 1992. "Properties of low–light level slow–scan detectors," Fluorescent and Luminescent Probes for Biological Activity.
Allen, M.J., et al., 1991. Scanning Microsc., 5:625.
Ambrose, W.P., et al., 1993. "Application of single molecule detection to DNA sequencing and sizing," Ber. Bunsenges. Phys. Chem., 97:1535:1542.
Andersson–Engels, S., et al., 1990. "Multicolor fluorescence imaging systems for tissue diagnosis," Proc. SPIE–Biomag. Two–Dimens. Spectrosc., 1205:179–89.
Ashworth, D., et al., "Transducer mechanisms for optical biosensors. Part 2: Transducer design", *Computer Methods and Programs in Biomedicine*, (1989), 30:21–31.
Aurup, H., et al., 1994. "Oligonucleotide duplexes containing 2'–amino–2'–deoxycytidines: thermal stability and chemical reactivity," Nucleic Acids Res., 22:20–4.
Arts et al., 1993. "Fusion of artificial membranes with mammalian spermatozoa," Eur. J. Biochem 217:1001–9.
Bains, W., 1991. "Hybridization methods for DNA sequencing," Genomics, 11:294–301.
Balzarini, 1984 "Thymidylate synthetase–deficient mouse FM3A mammary carcinoma cell line as a tool for studying the thymidine salvage pathway and the incorporation of thymidine analogues into host cell DNA"Biochim J, 217:245–52.
Barbin, A., et al. 1985. "Lack of miscoding properties of 7–(2–oxoethyl)guanine, the major vinyl chloride–DNA adduct," Cancer Res., 45:2440–4.
Bello et al, 1994. "Electroosmosis of polymer solutions in fused silica capillaries," Electrophoresis, 15:623–6.
Bezrukov, et al., 1994. "Counting polymers moving through a single ion channel," Nature. 370:279.

(List continued on next page.)

*Primary Examiner*—W. Gary Jones
*Assistant Examiner*—Janell E. Taylor
(74) *Attorney, Agent, or Firm*—Wolf, Greenfield & Sacks, P.C.

(57) ABSTRACT

The invention relates to methods and products for analyzing polymers. The polymers are analyzed by reconstructing sequence information from population data sets. The data sets include information about polymer dependent impulses arising from the polymers. The invention is also a method for linearly analyzing polymers by assessing the intensity of a signal arising from the polymer. The signal is generated as units and/or units specific markers pass a fixed station. The quantitative intensity of the signal is proportional to the number of units and/or unit specific markers giving rise to the signal.

35 Claims, 12 Drawing Sheets

OTHER PUBLICATIONS

Bezrukov, et al., 1997, "The charge state of an ion channel controls neutral polymer entry into its pore", Eur Biophys J., 26:471–476.

Bick. M. D.and Davisdon, R. L 1974. "Total substitution of bromodeoxyuridine for thymidine In the DNA of a broniodeoxyuddine–dependent cell line," Proc. Nat. Acad. Sci. USA. 71:2082–2086.

Bignold, L. P. 1987. "A novel polycarbonate (Nuclepore) merritirane demonstrates chernotaxis, unaffected by chernokinesis, of polymorphonuclear leukocyles in the Boyden chamber," J. of Immuno Methods., 105:275–280.

Bloom, L B., et al., 1996. "Dynamics of loading the beta sliding clarrip of DNA polymerase III onto DNA," J. Biol. Chem. 271:30699–708.

Bock, G. et al., 1985. "Photometric analysis of antilading reagents for immunofluorescence with laser and conventional illumination sources," J. of Histochemistry and Cytochemistry 33:699–705.

Bohmer, R. 1990. "Cell division analysis using bromodeoxyuridine–induced suppression of Hoechst 33258 fluorescence," Methods in Cell Biology 18:173–84.

Bustamante, C. 1991. "Direct observation and manipulation of single DNA molecules using fluorescence microscopy," Annu. Rev. Biophys. Chem. 20:415–46.

Buurman et al, 1992, "Fluorescence lifetime imaging using a conlocal laser scanning microscope," Scanning 14:155–59.

Cantor, C.R., et al., 1992. "Report on the sequencing by hybridization workshop," Genomics, 13:1378–1383.

Castro, A. and Shera, E. B. 1995. "Single–molecule electrophoresis," Anal. Chem. 67:3181–3186.

Chang, H. T. and Yeung, E. S. 1995. "Dynamic control to improve the separation performance in capillary electrophoresis," Electrophoresis. 16:2069–73.

Chen, D. and Dovichi, N. J. 1996. "Single–molecule detection in capillary electrophoresis: molecular shot noise as a fundamental limit to chernical analysis," Anal. Chern. 68:690696.

Chu et al, "Separation of large DNA molecules by contour–clamped homogeneous electric fields" Science e 234:1582.

Church, G. M. and Kieffer–Higgins, S. 1988. "Multiplex DNA sequencing," Science 240:185–88.

Clark, I., et al., 1993. "A study of sensitized lanthanide luminescence in an engineered calcium–binding protein," Anal. Biochem. 210:1–6.

Clegg, et al., 1993. "Observing the helical geometry of double–stranded DNA in solution by fluorescence resonance energy transfer," Proc. Natt. Acad. Sol. USA. 90:2994–98.

Clegg, R. M. 1995. "Fluorescence resonance energy transfer," Curr. Opin. Biotech. 6:103–110.

Crain, P. F. 1990. Mass Spectrom. Rev. 9:505–54.

Crissman and Steinkamp, 1990. "Detection of bromodeoxyuridine–labeled cells by differential fluorescence analysis of DNA fluorochromes," Methods in Cell Biology 33:199–206.

Davis, et al., 1992. "Rapid DNA sequencing based on single–molecule detection," Los Alamos Science. 20:280–6.

de Jong, P.J. et al., 1989. Cytogenet. Cell Genet. 51:985.

Ding, D. W. et al., 1972. Biopolymers 11:2109–2124.

Drmanac et al, 1989 "Sequencing of megabase plus DNA by hybridization: theory of the method" Genomics 4:114–128.

Eigen, M and Rigler, R. 1994. Sorting single molecules: applications to diagnostics and evolutionary biotechnology. Proc. Natf. Acad. Sci. USA. 91:5740–7.

el–Deiry., W.S., et al., 1993. WAFI, a potential mediator of p53 tumor suppression. Cell 75:817–825.

Faerber, P. and Scheft, K. H. 1971. Chem. Ber. 104:456–460.

Fairclough and Cantor, 1978. "The use of singlet–singlet energy transfer to study macromolecula assemblies," Methods in Enzym. 347–79.

Fan and Bard, 1995. "Electrochemical detection of single molecules," Science 267:871–4.

Fawcett et al., 1994. "Largescale chromosome sorting," Methods in Cell Biology 42:319–331.

Feinberg and Vogelsteln, 1983. "A technique for radiolabeling DNA restriction endonuclease fragments to high specific activity," Anal. Biochem. 132:6–13.

Feinberg and Vogelstein. 1984. "A technique for radiolabeling DNA restriction endonuclease fragments to high specific activity," (Addendum). Anal. Biochem. 137:2667.

Frey et al., 1995. "The nucleotide analog 2–aminopurine as a spectroscopic probe of nucleotide incorporation by the Klenow fragment of *Escherichia coli* polymerase I and bacteriophage T4 DNA polymerase."

Fu, T.J. et al., 1996. "Dynamics of DNA tracking by two–sliding–clamp proteins," EMBO J. 15:4414–22.

Gadella et al., 1993. "Fluorescence lifetime imaging microscopy (FLIM): spatial resolution of microstructures on the nanosecond time scale," Biophysical Chemistry. 48:221–239.

Gains et al., 1996. "A new method for measuring lymphocyte proliferation at the single–cell level in whole blood cultures by flow cytometry," J. of Immunological Meth. 195:63–72.

Garland and Moore, 1979. "Phosphorescence of protein–bound eosin and erythrosin: a possible probe for measurements of slow rotational motion," Biochem. J. 183, 561–572.

Gawrisch et al., 1993. "Interaction of peptide fragment 828–848 of the envelope glycoprotein of human immunodeficiency virus type I with lipid bilayers," Biochemistry 32:3112–18.

Gebeyehu et al., 1987. "Novel biotinylated nucleotide–analogs for labeling and colorimetric detection of DNA," Nucleic Acids Res. 15:4513–34.

Gibson, T.J. et al., 1987a. Gene, 53:275.

Gibson, T.J. et al., 1987b. Gene, 53:283.

Gill,D. 1979. "Inhibition of fading in fluorescence in microscopy of fixed cells," Experientia 35:400–1.

Gillam and Tener, 1986. N4–(6–aminohexyl) cytidine and –deoxycytidine nucleotides can be used to label DNA, Anal. Biochem. 157:199–207.

Giloh and Sedat, 1982. "Fluorescence microscopy; reduced photobleaching of rhodamine and fluorescein protein conjugates by n–propyl gallate," Science 217:12521255.

Glickman, B.W. 1985. Basic Life Sciences. 31:353–79.

Goodwin et al, 1995. "Spatial dependence of the optical collection efficiency in flow cytometry," Cytometry 21:133–144.

Gratton and Limkema, 1983. A continuously variable frequency cross–correlation phase fluorometer with picosecond resolution. Biophys. J. 44:315–325.

Griep, M. A. 1995. "Fluorescence recovery assay: a continuous assay for processive DNA polymerases applied specifically to DNA polymerase III holoenzyme," Anal. Biochem. 232:180–9.

Gueron, M. et al., 1967. J. Chem. Phys. 47:4077.

Haab and Mathies, 1995. "Single molecule fluorescence burst detection of DNA fragments separated by capillary electrophoresis," Anal. Chem. 67:3253–60.

Hamada and Fujita, 1983. "DAPI staining improved for quantitative cytotluorometry" Histochemistry 79:219–26.

Harding and Keller, 1992. "Single molecule detection as an approach to rapid DNA sequencing," Trends Biotechnol 10:55–57.

Harris and Kell, 1985 "On the dielectrically observable consequences of the diffusional motions of lipids and proteins in membranes. 2. Experiments with microbial cells, protoplasts; and membrane vesicles," Eur Biophysics. J. 13:11–24.

Herendeen and Kelly, 1996. "DNA polymerase III: running rings around the fork," Cell. 84:5–8.

Herman et al., "Fluorescence lifetime imaging in cell biology," Proceedings of Optical Diagnostics of Living Cells and Biofluids 2678:88–97.

Hogan et al., 1978. Proc. Natl. Acad. Sci. USA 75:195199.

Holzwarth, A. R. 1995. "Time–resolved fluorescence spectroscopy," Methods in Enzymology. 246:335–361.

Holzwarth et al., 1987. "Transient orientation of linear DNA molecules during pulsed field gel electrophoresis," Biopolymers 28:1043.

Huff et al., 1982. Enhancement of specific immunofluorescent findings with use of para–phenylenediamine mounting buffer. J. of Investigative Dermatology 78:449–50.

Hung et al., 1996. "Cyanine dyes with high absorption cross section as donor chromophores in energy transfer primers," Anal. Biochem. 243:15–27.

Ikehara et al., 1969b. Biochemistry 8:73&–43.

Jett et al., 1989. "High–speed DNA sequencing: an approach based upon fluorescence detection of single molecules," J. of Bio. Structure & Dynamics 7:301–9.

Johnson et al., 1982. Fading of immunofluorescence during microscopy: a study of the phenomenon and its remedy. J. of Immunological Methods 55:231–242.

Johnson et al., 1981. "A simple method of reducing the fading of immunofluorescence during microsocpy," J. of Immunological Methods 43:34950.

Ju et al., 1996a. "Cassette labeling for facile construction of energy transfer fluorescent primers," Nucleic Acid Res. 24:1144–8.

Ju et al., 1996b. "Energy transfer primers: a new fluorescence labeling paradigm for DNA sequencing and analysis," Nature Medicine. 2:246–9.

Jumppanen and Riekkola, 1995. "Influence of electrolyte composition on the effective electric field strength in capillary zone electrophoresis," Electrophoresis. 16:1441–4.

Kato and Yoshida, 1970. "Nondisjunction of chromosomes in a sychronized cell population initiated by reversal of colcemid Inhibition," Expl. Cell Res. 60:459–64.

Kinjo and Rigler, "Ultrasensitive hybridization analysis using fluorescence correlation spectroscopy," Nucleic Acids Research. 23:1795–1799.

Kirk et al., 1993. "Lanthanide–dependent perturbations of luminescence in indolylethylenediaminetetraacetic acid–lanthanide chelate," J. Phys. Chem. 97:10326–10340.

Klenchin et al, 1991. Electrically induced DNA uptake by cells in a fast process involving DNA electrophoresis Biophysical J. 60:804–11.

Korchemnaya et al., 1978. J. Anal Chem USSR (Eng. Transt.) 33:625.

Lakowicz and Berndt, 1991. Lifetime–selective fluorescence imaging using an RF phase–sensitive camera Rev. Sci. Instru. 62:3653.

Lang et al., 1968. Synthetic Procedures in Nucleic Acid Chemistty. 1:228, John Wiley & Sons, New York.

Langer et al., 1981. "Enzymatic synthesis of biotinlabeled polynucleotides: novel nucleic acid affinity probes," Proc. Nall. Acad. Sci. U.S.A. 78–6633–6637.

Lee et al., 1995. "A new approach to assay endo–type carbohydrases: bifluorescent–labeled substrates for glycoamidases and ceramide glycanases," Anal. Biochem. 230:31–6.

Lee et al. Nucleic Acids Res. 202471–2483.

Lee et al., 1994. "A fluorometric assay for DNA cleavage reactions characterized with HamHl restriction endonuclease," Anal. Biochem. 220:377–383.

Lee et al., 1995. "Characterization of endonucleolytic activity.of HIV–1 integrase using a fluorogenic substrate," Anal. Biochem. 227:295–301.

Lee et al, 1994 "Laser–induced fluorescence detection of a single molecule in a capillary" Anal Chem 66:4142–9

Lewotsky, K. 1994. "Hyperspectral Imaging: evolution of imaging spectrometry," SPIE OE/Rep Nov.:1–3.

Little et al., 1994. J. Am. Chem. Soc. 116:4893–4897.

Lockhart et al., 1996. "Expression monitoring by hybridization of high–density oligonucleotide arrays," Nature Biotechn 14:1675–1680.

Loros et al, 1989 "Molecular cloning of genes under control of the circadian clock in Neurospora,"Science 243:385–388.

Marcus and Robbins, 1963. "Viral inhibition in the metaphase–arrest cell," Proc. Natl. Acad. Sci. USA 50:1156–64.

Martin et al., 1994. Correlation between fusogenicity of synthetic modified peptides corresponding to the NH2–terminal extremity of simian immunodeficiency virus gp32 and their mode of insertion into the lipid bilayer: an infrared spectroscopy study. J. Wrol. 68:1139–48.

Matayoshi et al., 1990. "Novel fluorogenic substrates for assaying retroviral proteases by resonance energy transfer," Science. 247:954.

Matsumoto et al., 1981. "Light microscopic structure of DNA in solution studied by the 4'-6–diamidino–2–phenylindole staining method," J. MoL Biol. 152:501–516.

Maurizi et al., 1986. "Distances between active site probes in glutamine synthetase from *Escherichia coli* fluorescence energy transfer in free and in stacked dodecamers," Biochem. 25:141–151.

Mautner, H. G. 1956. J. Am. Chem. Soc. 78:5293.

Maxam and Gilbert, 1977. "A new method for sequencing DNA," Proc. Natl. Acad. Sci. USA. 74:5604.

Maymon & Neeck, 1988. "Optical system design alternatives for the Moderate–Resolution Imaging Spectrometer Tift (MODIS–T) for the Earth Observing System (EoS)" Proc.SPIE–Rec Adv.Sens, Radmtry Data Proc.Rem Sens 924:10–22.

McGown, L. B. 1989. "Fluorescence lifetime fiftering," Anal. Chem. 61:839A–847A.

Meffert and Dose, 1988. Uv–induced cross–linking of proteins to plasmid pBR322 containing 8–azidoadenine 2'–deoxyribonucleotides. FEBSLets. 239:190–4.

Meertz et al., 1995. "Single–molecule detection bytwo–photonexcited fluorescence," Optics Letters 20:2532–34.

Meinkoth, J. and Wahl, G. M. 1987. "Nick translation," Methods in Enzymology 152:91 94.

Menter et al., 1979. "Photochemistry of heparin–acridine orange complexes In solution," Photochemistry and Photobiology. 27:629–33.

Menter et al., 1978. "Kinetics of fluorescence fading of acridine orange–heparin complexes in solution," Photochemistry and Photobiology 27:629–633.

Miki et al., 1992. "Structure of actin observed by fluorescence resonance energy transfer spectroscopy," J. Muscle Res. Cell Motil. 13:132.

Miki and Lio, 1993. "Kinetics of structural changes of reconstituted skeletal muscle thin filaments observed by fluorescence resonance energy transfer," J. Biol. Chem. 268:7101–7106.

Moore et al., 1986. "The orientation, relaxation and reptation of DNA in orthogonal field, alternately–pulsed field gel electrophoresis: a linear dichrolsm study," Biopphys. J. 49:130a.

Morikawa, K., and Yangida, M. 1981. J. Biochem. 89:693.

Nakashima et al., 1992. IEEE Trans. Biomed. Engng. 39:26–36.

Nie et al, 1997, "Optical Detection of Single Molecules", *Annu Rev Biophys Biomol Struct*, 26:567–596.

Oida et al., 1993. "Fluorescence lifetime imaging microscopy (flimscopy): methodology development and application to studies of endosome fusion in single cells," Biophys. J. 64:676–685.

Onrust, R., and O'Donnell, M. 1993. J. Biol. Chem. 268:11766–72.

Pap et al., 1993. "Quantitation of the interaction of protein kinase C with diacylglycerol and phosphoinostitides by time–resolved detection of resonance energy transfer," Biochemistry 32:13310–17.

Paz–Elizur et al, 1996. "Beta*, a UV–inducible smaller form of the beta subunit sliding clamp of DNA polymerases III of *Escherichia coli*. 1. Gene expression and regulation,".J. Biol. Chem. 271:2482–90.

Peck et al, 1989. "Single–molecule fluorescence detection: autocorrelation criterion and experimental realization with phycoerythrin," Proc. Nati. Acad. Sci. USA 86.4087–4091.

Picciolo and Kaplan, 1984. "Reduction of fading of fluorescent reaction product for microphotometric quantitation," Advances in Applied Microbiology 30:197234.

Pillai, V. N. 1980. "Photoremovable protecting groups in organic synthesis," Synthesis. 1980:1.

Platt and Michael, 1983. "Retardation of fading and enhancement of intensity of immunofluorescence by p–phenylenediamine," J. of Histochemistry and Cytochemistry 31:840–42.

Poot and Hoehn, 1990. "Cell cycle analysis using continuous bromodeoxyuridine labeling and Hoescht 33258–ethidium bromide bivariate flow cytometry," Methods in Cell Biology 33:185–98.

Priore and Allen, 1979. Biopolymers 18:1809–1820.

Purmal et al, 1994. "5–Hydroxyprimidine deoxynudeoside triphosphates are more efficiently incorporated into DNA by exonuclease–free Klenow fragment.than 8–oxopurine deoxynucleoside triphosphates," Nucleic Acids Res. 22:3930–5.

Qu et al, 1996. "A role for melanin–concentrating hormone in the central regulation of feeding behaviour," Nature 380:243–247.

Rahan et al., 1965. Proc. Natl. Acad. Sci. USA 53:893.

Rampino.and Chrambach, 1990. "Apparatus for gel electrophoresis wfth continuous monitoring of individual DNA molecules by video epifluorescence microscopy," Anal. Biochem. 194:278–283.

Rao, 1968. "Mitotic synchrony in mammalian cells treated with nitrous oxide at high pressures," Science 160:774–6.

Rigby et al., 1977. "Labeling deoxyribonucleic acid to high specific activity In vitro by nick translation with DNA polymerase 1," J. Mol. Biol. 113:237–51.

Reddick et al., 1989. Phys. Rev. B 39:767–770.

Rodgers, M. A. J. and Firey, P. A. 1985. Photochem. Photobiol. 42:613.

Ronaghi et al, 1996 "Realtime DNA sequencing using detection of pyrophosphate release," Anal Biochem. 242:84–89.

Ross, P.D. and Scruggs, L. 1964. Bippolymers. 2:231–6.

Roychoudhury et al., 1979. "Influence of nucleotide sequence adjacent to duplex DNA termini on 3'–terminal labeling by terminal transferase," Nucleic Acids Res. 6:1323–1333.

Saha et al., 1993. "Time–resolved fluorescence of a new europium chelate complex: demonstration of highly sensitive detection of protein and DNA samples," J. Am. Chem. Soc. 115:11032–33.

Sahota and Khaledi, 1994. "Nanaqueous capillary electrophoresis," Anal. Chem 66:1141–6.

Saiki et al., 1988. "Primer–directed enzymatic amplif ication of DNA with a thermostable DNA polymerase," Science 239:487–91.

Sanger et al., 1977. "DNA sequencing with chain–terminating inhibitors," Proc. Nall. Acad. Sci. USA. 74:5463–7.

Sase et al., 1995. "Real time imaging of single fluorophores on moving actin with an epifluorescence microscope," Bidphys. J. 69:323–8.

Schellman and Jensen, 1987. "Optical spectroscopy of oriented molecules," Chem. Rev.. 87:1359.

Schott, J. R. 1989. "Remote sensing of the Earth: A synoptic view," Phys Today Sep.:72–79.

Selvin et al., 1994. "Luminescehce resonance energy transfer," J. Am. Chem. Soc. 11 6:6029~30.

Shera et al., 1990. "Detection of single fluorescent molecules," Chem. Phys. Letts. 174:553–57.

Shikmus et al., 1986. "Synthesis and characterization of biotin–labeled nucleotide analogs," DNA. 5:247–55.

Skaliter et al., 1996. "Beta* a UV–inducible shorter form of the beta subunit of DNA polymerase III of *escherichia coli*. 11. Overproduction, purification, and activity as a polymerase processivity clarnp," J. Biol. Chem. 271:2491–6.

Smirnov et al, 1996 "Sequencing oligonucleotides by exonuclease digestion and delayed extraction matrix–assisted laser desorption ionization time–of–flight mass spectrometry," Anal. Biochem. 238:19–25.

Smith et al, 1990 "Isolation and structure of an arrestin gene from Drosophila" Proc Nat Acad Sci USA 87:1003–07.

Smith, L.M., et al., 1986. "Fluorescence detection in automated DNA sequence analysis," Nature. 321:674–9.

Spatz and Grabig, 1983. "Reduced fading of fast blue fluorescence in the brain of the guinea–pig by treatment with sodium–nitroprusside," Neuroscience Letters 38:1–4.

Steinberg, I.Z. 1971. Annu.Rev.Biochem. 40:83.

Stewart et al., 1968. "Chinese hamstercell monolayer cell cultures," Exp. Cell Res. 49:293–299.

Stryer, L. 1978. Annual Review of Biochem. .47:819.

Stubblefield, 1968. "Synchronization methods for mammalian cell cultures," Methods in Cell Physiology, 3:25–43, Academic Press, New York.

Sturm and Weill, 1989. "Direct of observation of DNA chain orientation and relaxation by electric birefringence: implications for the mechanism of separation during pulsed–field gel electrophoresis," Phys. Rev. Lett. 62:1484.

Taliani et al, 1996. "A continuous assay of hepatitis C virus protease based on resonance energy transfer dipeptide substrates," Anal Biochem. 240:60–7.

Taylor, D. L and Salmon, E D. 1989. Methods In Cell Biol. 29:207–37.

Taylor et al., 1981. "Detection of actin assembly by fluorescence energy transfer," J. Cell Biol. 89:363.

ter Beest and Hoekstra, 1993. "Interaction of myelin basic protein with artifical membranes. Parameters governing binding, aggregation and dissociation," Eur. J. Biochem. 211:689–96.

Uchiyama et al., 1996. "Detection of undegraded oligonucleotides in vivo by fluorescence resonance energy transfer," J. Biol. Chem. 271:380–84.

Ueda et al., 1974. Chem. Pharm. Bull. (Tokyo). 22:2377–2382.

Valnes & Brandtzaeg,.1985.."Retardation of immunofluorescence fading during microscopy," J. of Histochem. and Cytochemistry 33:755–761.

van Hulst et al., 1993. Appl. Phys. Lett. 62:461.

Vaughan and Weber, 1970. "Oxygen quenching of pyrenebutyric acid fluorescence in water. A dynamic probe of the microenvironment," Biochemistry 9:464–473.

Waggoner, 1995. "Covalent labeling of proteins and nucleic acids with fluorophores," Methds. in Enzym. 246:362–373.

Wang et al., 1995. "Discovery of adrenomedullin in rat ischernic cortex and evidence for its role in exacerbating focal brain ischemic damage," Proc. Nall. Acad. Sci. USA 87:10031007.

Wang et al, 1990. "Time–resolved fluorescence microscopy using multichannel photon counting," Appl. Spectr. 44:25.

Wang et al., 1995. "Rapid sizing of short tandem repeat alleles using capillary array electrophoresis and energy–transfer fluorescent primer," Anal. Chem. 67:1197–203.

Ward and Reich, 1969. Fluorescence studies of nucleotides and polynucleotides. 244:1228–1237.

Weimann et al., 1995. "Primer design for automated DNA sequencing utilizing T7 DNA polymerase and internal labeling with fluorescein-1 5–dATP," BioTechniques 18:688–97.

Wilkinson et al., 1995. Identification of mRNAs with enhanced expression in ripening strawberry fruit using polymerase chain reaction differential display. Plant Mol. Biol, 27:1097–1108.

Wittwer et al, 1997. "Continuous fluorescence monitoring of rapid cycle DNA amplification," Biotechn. 22:130–1, 1348.

Wooley & Mathies, 1995. "Ultra–high–speed DNA sequencing using capillary electrophoresis chips," Anal. Chem. 67:3676–3680.

Woronicz et al, 1994. "Requirement for the orphan steroid receptor Nur77 in apoptosis of T–cell hybridomas," Nature 367:277–281.

Wu et al., 1981. Proc. Nati. Acad. Sci. USA 78:6808–6811.

Wu and Brand 1994. "Resonance energy transfer: methods and applications," Anal. Biochem. 218:1–13.

Wunderlich & Peyk, 1969. "Antimitotic agents and macronuclear division of ciliates. 11. Endogenous recovery from colchicine and colcemid–a new method of synchronization," Tetrahymena pyriformis GL Expl. Cell Res. 57:142–4.

Yamaoka, K. and Matsuda, K. 1981. Macromolecules 14:595–601.

Yamaoka, K. and Charney, E. 1973. Macromolecules 6:66–76.

Vane et al, 1988. "Comparison of laboratory calibrations of the Airborne Visible/Infrared Imaging Spectrometer (AVRIS) at the beginning and end of the first flight season," Proc SPIE–Recent Adv Sensors, Radiometry Data Proc Remote Sens 924:168–178.

Zweig, 1973. "Photochemical generation of stable fluorescent compounds (photofluorescence)," Pure and Applied Chemistry 33:389–410.

Wu et al., "Fast Multisite Optical Measurement of Membrane Potential," Department of Physiology, Yale University School of Medicine, New Haven, CT, USA, Chapter Thirty, pp. 389–404.

Franklin et al., "A New Technique for Retarding Fading of Fluorescence: DPX–BME," Stain Technology, vol. 60, No. 3, 1985, pp. 125–135.

Mal'tsev et al., "Optimization of the Chromatographic Analysis of Amino Acids," Institute of High–Molecular––Weight Compounds, Academy of Sciences of the USSR, Leningrad. Translated from Zhurnal Analiticheskoi Khimii, vol. 33, No. 4, pp. 798–807, Apr., 1978.

Alexancer et al., "The Reaction of Oxidizing Agents with Wool," Biochem., 1951, vol. 49, pp. 129–138.

Bukrinskaya et al., "Synthesis of Protein in Paramyxovirus–Infected Cells of Susceptible and Resistant Lines at the Early Stage of Infection," D.I. Ivanovskii Institute of Virology, Academy of Medical Sciences of the USSR, Moscow, Translated From Biokhimiya, vol. 35, No. 3, pp. 516–523, May–Jun. 1970.

Wang et al, "High–resolution capillary array electrophoretic sizing of multiplexed short tandem repear loci using energy–Transfer fluorescent primers," Electrophoresis, 1996, vol. 17, pp. 1485–1490.

Smith et al., "Observation of Individual DNA Molecules Undergoing Gel Electrophoresis," Science, vol. 243, Jan. 1989, pp. 203–206.

Schwartz et al., "Conformational dynamics of individual DNA molecules during gel electrophoresis," Nature, vol. 338, Apr. 1989, pp. 520–522.

Gurrieri et al., "Imaginf of Kinked Configurations of DNA Molecules Undergoing Orthogonal Field Alternating Gel Electrophoresis by Fluorescence Microscopy," Biochemistry, 1990, vol. 29, pp. 3396–3401.

Morozov et al., "New polyacrylamide gel–based methods of sample preparation for optical microscopy: immobilization of DNA molecules for optical mapping," Journal of Microscopy, 1996, vol. 183, pp. 205–214.

Meng et al., "Inhibition of Restriction Endonuclease Activity by DNA Binding Fluorochromes," Dynamics, vol. 13, Issue No. 6, 1996, pp. 945–951.

Meng et al., "Optical mapping of lambda bacteriophage clones using restriction endonuclease," *Nature Genetics*, vol. 9, Apr. 1995, pp. 432–438.

Printout from Kivo Genetics Web Page.

Article by Robert A. Metzger from *Wired*, Nov. 1998, p. 4.

Davis et al., *Genet Anal Tech Appl* 1991, 8(1) pp. 1–7.

Glazer, *Curr. Opin. Biotechnol.* 1997, 8(1) pp. 94–102.

Houseal et al., *Biophys J* 1989, 56(3) pp. 507–516.

Marra et al., *Genome Res* 1996, 6(11) pp. 1118–1122.

Naktinis et al., *Cell* 1996, 84(1) pp. 137–145.

Soper et al., *J. Chromotagr A* 1999, 853(1–2) pp. 107–120.

Soper et al., *Anal Chem* 1998, 70(19) pp. 4036–43.

Ferreira et al., *ACS* 1995, 28, pp. 7107–7114.

Nguyen et al., *Anal Chem* 59, 2158–2161.

Periasamy et al., *J. of Computer Assisted Microscopy*, 1994, 6, pp. 1–26.

Kasianowicz et al., *Proc Natl Acad Sci USA*, 93:13770–13773, Nov. 1996.

Lee et al., *J Phys II* France, 6:195–204 (Feb. 1996).

Sung et al., *Physical Review Letters*, 74(4):783–788 (Jul. 22, 1996).

Morozov et al. "New polyacrylamide gel–based methods of sample preparation for optical microscopy: immobilization of DNA molecules for optical mapping" *Journal of Microscopy*, Sep. 1996 pp. 205–214.

Parsegian et al., *Bioscience Reports*, 15(6):503–514 (1995).

Kasianowica, Abstract, Polymer Transport in the Alpha–Hemolysin Ion Channel; 6.

Bathori et al., Abstract, Th–AM–K8: DNA can be translocated across planar bilayer membranes containing Mitochondrial porin.

Haugland, Handbook of Fluorescent Probes and Research Chemicals, Sixth Edition, Chapters 8 and 9, 1996, pp. 143–200.

Alper, J., et al., "From the bioweapons trenches, new tools for battling microbes", *Science*, (1999), 248:5421:1754–5.

Nie, et al., "Probing individual molecules with confocal fluorescence microscopy", Science, ((1994), 266:5187:1018–1021.

* cited by examiner

FIG. 6

```
5'ACTGACGTACGTACGTACGT'3
5'ACTGACGTACGTACGTACGT'3
5'ACTGACGTACGTACGTACGT'3
5'ACTGACGTACGTACGTACGT'3
```

ORIGINAL SEQUENCE →

```
5'ACTGACGTACGTACGTACGT'3
```

RESULTING FLUORESCENCE IMAGE

EXAMPLE 1 AND MIGRATION OF DNA THROUGH NANOCHANNEL PLATE

EXAMPLE 3 OF HEXAGONALLY PACKED
BEADS AS RESTRICTIVE NANOSTRUCTURES

METHODS OF ANALYZING POLYMERS USING ORDERED LABEL STRATEGIES

RELATED APPLICATIONS

This application claims priority to U.S. Provisional Patent Application Nos. 60/096,666, filed Aug. 13, 1998 and 60/120,662, filed Aug. 13, 1998 and is a continuation in part of U.S. patent Ser. No. 09/134,411 filed on Aug. 13, 1998, currently pending, which is a 371 of PCT/US98/03024 filed on Feb. 11, 1998, which claims priority to U.S. Provisional Patent Application Nos. 60/096,687, filed May 5, 1997 and 60/037,921, filed Feb. 12, 1997 the entire contents of which are hereby incorporated by reference.

FIELD OF THE INVENTION

The present invention relates to methods and products for analyzing polymers. In particular, the methods are based on generation of information from a data set of polymer dependent impulses arising from polymers which have been labeled according to an ordered strategy. The information generated relates to many aspects of the polymer such as the length of the polymer, the composition of units within the polymer, the order of units in the polymer, and the sequence or partial sequence of units in the polymer. The invention also relates to methods for intensity based analysis.

BACKGROUND OF THE INVENTION

Polymers are involved in diverse and essential functions in living systems. The ability to decipher the function of polymers in these systems is integral to the understanding of the role that the polymer plays within a cell. Often the function of a polymer in a living system is determined by analyzing the structure and determining the relation between the structure and the function of the polymer. By determining the primary sequence in a polymer such as a nucleic acid it is possible to generate expression maps, to determine what proteins are expressed, and to understand where mutations occur in a disease state. Because of the wealth of knowledge that may be obtained from sequencing of polymers many methods have been developed to achieve more rapid and more accurate sequencing methods.

In general DNA sequencing is currently performed using one of two methods. The first and more popular method is the dideoxy chain termination method described by Sanger et al. (1977). This method involves the enzymatic synthesis; of DNA molecules terminating in dideoxynucleotides. By using the four ddNTPs, a population of molecules terminating at each position of the target DNA can be synthesized. Subsequent analysis yields information on the length of the DNA molecules and the base at which each molecule terminates (either A, C, G, or T). With this information, the DNA sequence can be determined. The second method is Maxam and Gilbert sequencing (Maxam and Gilbert, 1977), which uses chemical degradation to generate a population of molecules degraded at certain positions of the target DNA. With knowledge of the cleavage specificities of the chemical reactions and the lengths of the fragments, the DNA sequence is generated. Both methods rely on polyacrylamide gel electrophoresis and photographic visualization of the radioactive DNA fragments. Each process takes about 1–3 days. The Sanger sequencing reactions can only generate 300–800 bases in one run.

Methods to improve the output of sequence information using the Sanger method also have been proposed. These Sanger-based methods include multiplex sequencing, capillary gel electrophoresis, and automated gel electrophoresis. Recently, there has also been increasing interest in developing Sanger independent methods as well. Sanger independent methods use a completely different methodology to realize the base information. This category includes scanning electron microscopy (STM), mass spectrometry, enzymatic luminometric inorganic pyrophosphate detection assay (ELIDA) sequencing, exonuclease sequencing, and sequencing by hybridization.

Further, several new methods have been described for carboxy terminal sequencing of polypeptides. See Inglis, A. S., Anal. Biochem. 195:183–96 (1991). Carboxy terminal sequencing methods mimic Edman degradation but involve sequential degradation from the opposite end of the polymer. See Inglis, A. S., Anal. Biochem. 195:183–96 (1991). Like Edman degradation, the carboxy-terminal sequencing methods involve chemically induced sequential removal and identification of the terminal amino acid residue.

More recently, polypeptide sequencing has been described by preparing a nested set (sequence defining set) of polymer fragments followed by mass analysis. See Chait, B. T. et al., Science 257:1885–94 (1992). Sequence is determined by comparing the relative mass difference between fragments with the known masses of the amino acid residues. Though formation of a nested (sequence defining) set of polymer fragments is a requirement of DNA sequencing, this method differs substantially from the conventional protein sequencing method consisting of sequential removal and identification of each residue. Although this method has potential in practice it has encountered several problems and has not been demonstrated to be an effective method.

SUMMARY OF THE INVENTION

The present invention relates in some aspects to methods and products for analyzing polymers. In particular the invention in one aspect is a method for identifying information about a polymer such as its sequence, length, order of bases etc., by obtaining polymer dependent impulses from a population of polymers and comparing the polymer dependent impulses to determine unit specific information about the polymers.

Recently, methods for analyzing polymers based on unit specific information about the polymer have been developed. Such methods are described in co-pending PCT patent application No. PCT/US98/03024 and U.S. Ser. No. 09/134,411 filed Aug. 13, 1998, the entire contents of which are hereby incorporated by reference. The method for analyzing polymers described in PCT/US98/03024 and 09/134,411 is based on the ability to examine each unit or unit specific marker of a polymer individually. By examining each unit or unit specific marker individually the type of units and the position of the units on the backbone of the polymer can be identified. This can be accomplished by positioning a labeled unit or unit specific marker at a station and examining a change which occurs when that labeled unit or unit specific marker is proximate to the station. The change can arise as a result of an interaction that occurs between the unit or unit specific marker and the station or a partner and is specific for the particular unit or unit specific marker. For instance if the polymer is a nucleic acid molecule and a T is positioned in proximity to a station a change which is specific for a T could occur. If on the other hand, a G is positioned in proximity to a station then a change which is specific for a G could occur. The specific change which occurs, for example, depends on the station used, the type of polymer being studied and/or the label used. For instance the change may be an electromagnetic signal which arises as a result of the interaction.

Methods for analyzing polymers based on unit specific information about the polymer involves the detection of polymer dependent impulses from a plurality of polymers to produce a data set of information. The data set can be compared to provide specific information about the polymer such as the composition of units in the polymer, the length of the polymer, the presence of specific sequences in the polymer, and even the entire sequence of the units in the polymer.

In one aspect the invention is a method for generating unit specific information about a polymer. The method includes the steps of obtaining polymer dependent impulses for a plurality of labeled polymers, comparing the polymer dependent impulses obtained from each of the plurality of labeled polymers, determining unit specific information about the polymers based upon comparing the polymer dependent impulses. Preferably the polymer dependent impulses arise from unit specific markers of less than all units of the polymers. In an embodiment the polymer dependent impulses arise from at least two unit specific markers of the polymers.

The plurality of polymers may be any type of polymer but preferably is a nucleic acid. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

The polymer dependent impulses provide many different types of structural information about the polymer. For instance the obtained polymer dependent impulses may include an order of polymer dependent impulses or the obtained polymer dependent impulses may include the time of separation between specific signals or the number of specific polymer dependent impulses. The obtained polymer dependent impulses may indicate the sequence of units of the polymer.

In one important embodiment the polymer dependent impulses are obtained by moving the plurality of polymers linearly past a signal generation station.

According to another embodiment the unit specific markers are nucleic acid probes. In another embodiment the unit specific markers are peptide nucleic acid probes.

The unit specific markers may identify a single unit of a polymer or multiple units of a polymer. When the polymer is a nucleic acid the unit specific marker may be a nucleic acid probe. In one embodiment the unit specific marker is a nucleic acid probe having at least two base pairs. In another embodiment the unit specific marker is a nucleic acid probe having at least three base pairs.

According to another aspect of the invention a method for sequencing a polymer of linked units is provided. The method includes the steps of obtaining polymer dependent impulses from a plurality of overlapping polymers, at least a portion of each of the polymers having a sequence of linked units identical to the other of the polymers, and comparing the polymer dependent impulses from an overlapping portion of each of the plurality of polymers to obtain a sequence of linked units which is identical in the plurality of polymers.

The polymer dependent impulses may be detected by many means. A preferred method of detection is optical detection.

The plurality of polymers may be any type of polymer but preferably is a nucleic acid. Preferably the nucleic acids are labeled with an agent selected from the group consisting of an electromagnetic radiation source, a quenching source and a fluorescence excitation source. In one embodiment the plurality of polymers is a homogenous population. In another embodiment the plurality of polymers is a heterogenous population. The polymers can be labeled, randomly or non randomly. Different labels can be used to label different linked units to produce different polymer dependent impulses.

The polymer dependent impulses provide many different types of structural information about the polymer. For instance the obtained polymer dependent impulses may include an order of polymer dependent impulses or the obtained polymer dependent impulses may include the time of separation between specific signals or the number of specific polymer dependent impulses. The obtained polymer dependent impulses may indicate the sequence of units of the polymer.

In one important embodiment the polymer dependent impulses are obtained by moving the plurality of polymers linearly past a signal generation station.

According to another embodiment the unit specific marker is a nucleic acid probe. In another embodiment the unit specific markers is a peptide nucleic acid probe. In another embodiment, the unit specific marker is a peptide.

The unit specific markers may identify a single unit of a polymer or multiple units of a polymer. When the polymer is a nucleic acid the unit specific marker may be a nucleic acid probe. In one embodiment the unit specific marker is a nucleic acid probe having at least three base pairs. In another embodiment the unit specific markers are three base pair nucleic acid probes.

The invention in another aspect is a kit for labeling polymers. The kit includes a container housing a series of distinct nucleic acid probes; wherein the series of nucleic acid probes is a set of multiple base pair probes. Preferably the multiple base pair probes are selected from the group consisting of two base pair probes, three base pair probes, four base pair probes, and five base probes.

In one embodiment the container is a single container having a plurality of compartments, each housing a specific labeled probe. In another embodiment the container is a plurality of containers.

The kit in one embodiment also includes instructions for labeling the nucleic acid probes.

The distinct nucleic acid probes are labeled in one embodiment. Preferably the nucleic acid probes are labeled with an agent selected from the group consisting of an electromagnetic radiation source, a quenching source and a fluorescence excitation source. In one embodiment the plurality of polymers is a homogenous population. In another embodiment the distinct nucleic acid probes are three base pair probes. In another embodiment the distinct nucleic acid probes are four base pair probes. In yet another embodiment the distinct nucleic acid probes are five base pair probes.

The invention in other aspects relates to methods and products for linear analysis of polymers using an intensity based method for identifying information about the polymer such as its sequence, length, order of bases etc. The methods can be accomplished using intensity based measurements combined with the ordered labeling strategy discussed above.

One aspect of linear analysis involves the movement of the polymer past a fixed station in such a manner as to cause a signal that provides information about the polymer to arise. According to an aspect of the invention it was discovered that information about the polymer can be determined by quantitatively measuring intensity of the signal arising at the station. The signal arises from the polymer as a result of the units of the polymer passing the fixed station. In some cases all of the units may cause the generation of a signal and in other cases less than all of the units produce the signal. The total intensity of the signal is proportional to the number of units or unit specific markers which generate a signal as they pass the fixed station. If the signal arises from every unit of the polymer then the intensity of the signal is proportional to the number of units in the polymer. If the signal arises from less than all of the units or unit specific markers of the polymer then the intensity of the signal is proportional to that number of units or unit specific markers causing generation of the signal. The number of units or unit specific markers indicated by the intensity can be used to determine information about the polymer such as the composition of units in the polymer, the length of the polymer, the presence of specific sequences in the polymer, and even the entire sequence of the units in the polymer.

The invention in another aspect is a method for analyzing a polymer by linearly moving a labeled polymer with respect to a fixed station, obtaining a signal from the labeled polymer as the labeled polymer passes the fixed station, wherein the signal is an electromagnetic radiation signal arising from an interaction between at least two distinct labeled unit specific markers and determining a quantitative measure of intensity of the signal to analyze the polymer.

The intensity of the signal provides various types of structural information about a polymer, depending on how the polymer is labeled. In one embodiment each unit of the labeled polymer is labeled with a unit specific marker and the quantitative measure of intensity of the signal indicates the length of the polymer. In another embodiment less than all units of the polymer are labeled with at least one unit specific marker and the quantitative measure of intensity of the signal indicates the number of labeled unit specific markers present in the polymer.

The fixed station which gives rise to the signal when the labeled polymer interacts with the station in one embodiment is an electromagnetic radiation source. In another embodiment the fixed station is a radiation source.

More than one polymer may be analyzed to generate a data set representative of a population of polymers. Thus in one embodiment a plurality of polymers are analyzed simultaneously to produce a plurality of signals, one signal for each polymer, and further comprising the step of comparing the intensities of the signals to analyze the polymers.

The labeled polymer may be labeled with a unit specific marker. In one embodiment the unit specific marker is a peptide nucleic acid probe. In another embodiment the unit specific marker is a series of distinct nucleic acid probes selected from the group consisting of two base pair probes, three base pair probes, four base pair probes, and five base pair probes. In yet another embodiment the unit specific marker is a fluorescent probe.

According to another embodiment the labeled polymer is labeled with a plurality of unit specific markers, wherein at least one unit specific marker includes a fluorophore which emits light at a first wavelength and at least one unit specific marker which includes a fluorophore which emits light at a second wavelength. In another embodiment the at least one unit specific marker which includes the fluorophore which emits light at the first wavelength is attached to end units of the polymer and wherein the at least one unit specific marker which emits light at the second wavelength is attached to an internal unit of the polymer.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 6 illustrates the generation of sequence information from the sorted data.

BRIEF DESCRIPTION OF THE SEQUENCES

Figure 1:
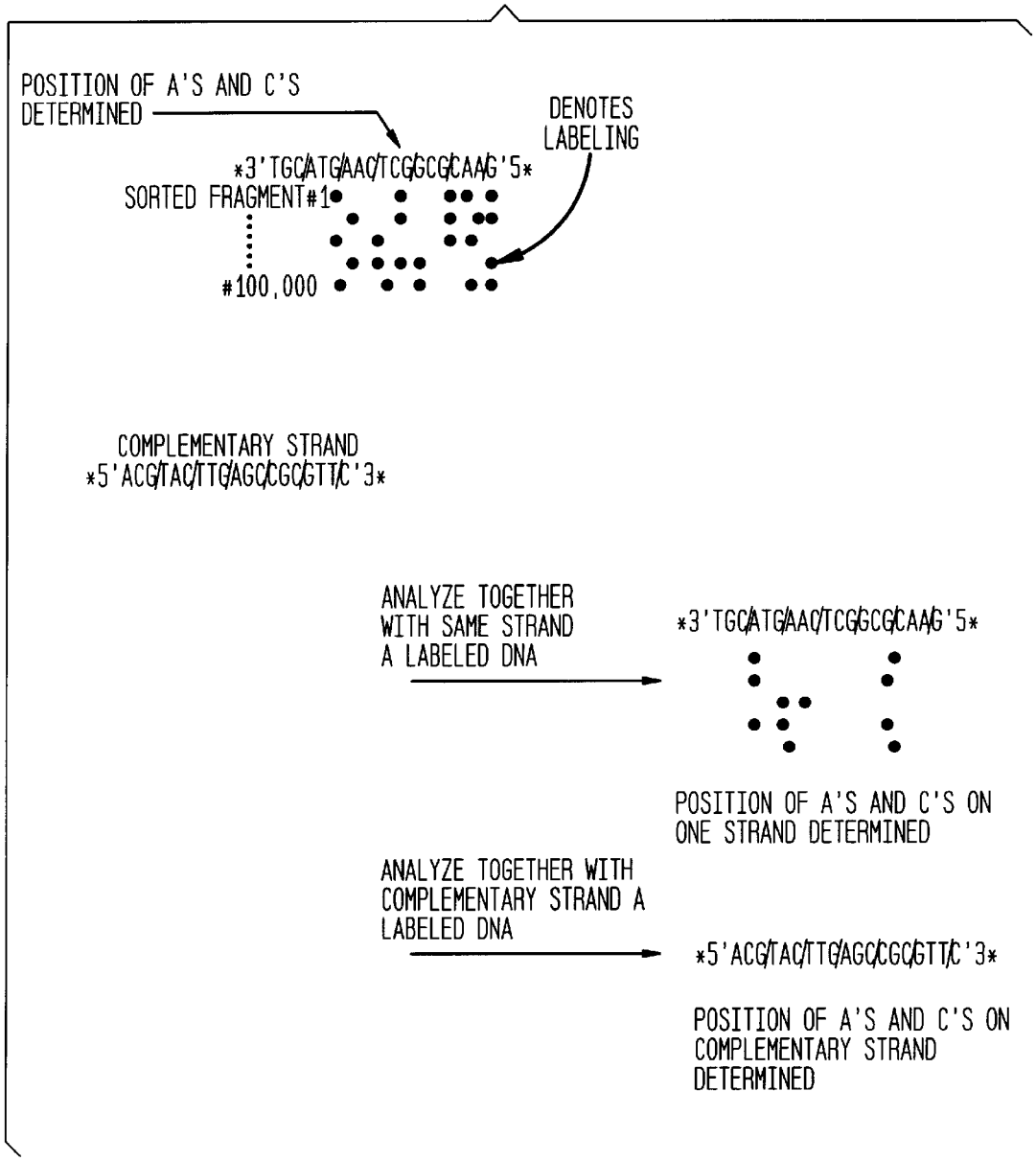
FIG. 1 shows a schematic of a random labeling method in which two differently labeled DNA samples are used.

SEQ. ID. NO. 1 is a hypothetical nucleic acid sequence.
SEQ. ID. NO. 2 is a hypothetical nucleic acid sequence.
SEQ. ID. NO. 3 is a hypothetical nucleic acid sequence.

DETAILED DESCRIPTION OF THE INVENTION

The invention is a method for analyzing polymers based on a compilation of data obtained from incomplete labeling of the polymers. The methods can be performed using data generated from single unit labels or multiple unit labels (both referred to herein as unit specific markers), single stranded polymers, double stranded polymers, or combinations thereof.

One advantage of the invention is that the method provides a rational means of deciphering incomplete labeling schemes into information, e.g., sequence information about the polymer, without requiring the labeling of each unit within a polymer. There are certain physical limits to labeling polymers such as DNA, which make it very difficult to completely label every nucleotide in a strand of DNA. For instance, in a single strand of DNA, the replacement of the native bases by fluorescently labeled bases is hindered by the major groove and base-to-base steric interactions of fluorophores derivatized to adjacent bases. Stack hindrance problems have made common methods of DNA analysis such as exonuclease sequencing difficult to perform. The methods of the invention provide the ability to decipher incomplete labeling schemes through various labeling methods to generate sequence information about polymers rapidly and accurately. The methods of the invention also provide enhanced resolution over prior art sequencing methods.

In one aspect the invention is a method for generating unit specific information about a polymer. The method includes the steps of obtaining polymer dependent impulses for a plurality of labeled polymers, comparing the polymer dependent impulses of the plurality of labeled polymers, determining unit specific information about the polymers based upon the polymer dependent impulses. Preferably the polymer dependent impulses arise from unit specific markers of less than all units of the polymers.

As used herein the term "unit specific information" refers to any structural information about one, some, or all of the units of the polymer. The structural information obtained by analyzing a polymer according to the methods of the invention may include the identification of characteristic properties of the polymer which (in turn) allows, for example, for the identification of the presence of a polymer in a sample or a determination of the relatedness of polymers, identification of the size of the polymer, identification of the proximity or distance between two or more individual units or unit specific markers a polymer, identification of the order of two or more individual units or unit specific markers within a polymer, and/or identification of the general composition of the units or unit specific markers of the polymer. Since the structure and function of biological molecules are interdependent, the structural information can reveal important information about the function of the polymer.

The methods of the invention are performed by detecting signals referred to as polymer dependent impulses. A "polymer dependent impulse" as used herein is a detectable physical quantity which transmits or conveys information about the structural characteristics of a unit specific marker of a polymer. The physical quantity may be in any form which is capable of being detected. For instance the physical quantity may be electromagnetic radiation, chemical conductance, electrical conductance, etc. The polymer dependent impulse may arise from energy transfer, quenching, changes in conductance, radioactivity, mechanical changes, resistance changes, or any other physical changes. Although the polymer dependent impulse is specific for a particular unit specific marker, a polymer having more than one of a particular labeled unit specific marker will have more than one identical polymer dependent impulse. Additionally, each unit specific marker of a specific type may give rise to different polymer dependent impulses if they have different labels. In some embodiments when intensity of a signal is being measured, the polymer dependent impulse is an optical signal The method used for detecting the polymer dependent impulse depends on the type of physical quantity generated. For instance if the physical quantity is electromagnetic radiation then the polymer dependent impulse is optically detected. An "optically detectable" polymer dependent impulse as used herein is a light based signal in the form of electromagnetic radiation which can be detected by light detecting imaging systems. In some embodiments the intensity of this signal is measured. When the physical quantity is chemical conductance then the polymer dependent impulse is chemically detected. A "chemically detected" polymer dependent impulse is a signal in the form of a change in chemical concentration or charge such as an ion conductance which can be detected by standard means for measuring chemical conductance. If the physical quantity is an electrical signal then the polymer dependent impulse is in the form of a change in resistance or capacitance.

A "plurality of polymers" is at least two polymers. A plurality of polymers in one embodiment is at least 50 polymers and in another embodiment is at least 100 polymers.

The polymer dependent impulses may provide any type of structural information about the polymer. For instance these signals may provide the entire or portions of the entire sequence of the polymer, the order of polymer dependent impulses, or the time of separation between polymer dependent impulses as an indication of the distance between the units or unit specific markers.

The polymer dependent impulse arises from a detectable physical change in the unit specific marker of the polymer or the station (or environment surrounding the station). As used herein a "detectable physical change" in the unit specific marker of the polymer or the station is any type of change which occurs in the unit specific marker of the polymer or the station as a result of exposing the unit specific marker to the station. Once the unit specific marker is exposed to the station a detectable signal or polymer dependent impulse is created. The station may be for instance, an interaction station or a signal generation station. The type of change that occurs in the station or the unit specific marker to produce the detectable signal or polymer dependent impulse depends on the type of station and the type of unit specific marker. Several examples of station-unit specific marker combinations which undergo a change to produce a detectable signal are discussed herein for exemplary purposes. Those of skill in the art will be able to derive other station-unit specific marker combinations that fall within the scope of the invention.

The polymer dependent impulses are obtained by interaction which occurs between the unit specific marker of the polymer and a signal generation station or the environment at a signal generation station. A "signal generation station" as used herein is a station that is an area where the unit specific marker interacts with the station or the environment to generate a polymer dependent impulse. In some aspects of the invention the polymer dependent impulse results from contact in a defined area with an agent selected from the group consisting of electromagnetic radiation, a quenching source, and a fluorescence excitation source which can interact with the unit specific marker to produce a detectable signal or polymer dependent impulse. In other aspects the polymer dependent impulse results from contact in a defined area with a chemical environment which is capable of undergoing specific changes in conductance in response to an interaction with a molecule. As a molecule with a specific structure interacts with the chemical environment a change in conductance occurs. The change which is specific for the particular structure may be a temporal change, e.g., the length of time required for the conductance to change may be indicative that the interaction involves a specific structure or a physical change. For instance, the change in intensity of the interaction may be indicative of an interaction with a specific structure. In other aspects the polymer dependent impulse results from changes in capacitance or resistance caused by the movement of the unit specific marker between microelectrodes or nanoelectrodes positioned adjacent to the polymer unit specific marker. For instance the signal generation station may include microelectrodes or nanoelectrodes positioned on opposite sides of the polymer unit specific marker. The changes in resistance or conductance which occur as a result of the movement of the unit specific marker past the electrodes will be specific for the particular unit specific marker.

The invention also relates to a method of analyzing polymers using linear analysis to generate an optical signal, wherein the intensity of the optical signal provides information about the polymer to analyze the polymer. The generated optical signal may be any type of electromagnetic radiation signal for which intensity can be determined (e.g., fluorescence, radiation, etc.).

As used herein "similar polymers" are polymers which have at least one overlapping region. Similar polymers may be a homogeneous population of polymers or a heterogenous population of polymers. A "homogeneous population" of polymers as used herein is a group of identical polymers. A "heterogenous population" of similar polymers is a group of similar polymers which are not identical but which include at least one overlapping region of identical units. An overlapping region typically consists of at least 10 contiguous nucleotides. In some cases an overlapping region consists of at least 11, 12, 13, 14, 15, 16, 17, 18, 19, 20, 21, or 22 contiguous nucleotides.

A "plurality of labeled polymers" refers to two or more similar polymers which are labeled intrinsically or extrinsically. Preferably a plurality of similar polymers is 50 or more similar polymers. More preferably a plurality of similar polymers is 100 or more similar polymers.

A "data set" as used herein is a set of information defining the polymer dependent impulses generated by similar polymers. The data set is analyzed as discussed above and the method of analysis used depends on the type of labeling scheme used to generate the labeled polymers.

Nucleic acid sequencing is a particularly preferred embodiment of the methods of the invention. Currently, less than 5% of the human genome has been sequenced. This translates into a small fraction of the ideal in human sequence knowledge, which is the sequence of all individuals. For instance, for the human population, there are $1.4 \times 10^{19}$ (5 billion people$\times 3 \times 10^9$ bases/person). So far, only $2 \times 10^{-10}$ percent of all human genetic information is known. The rate of sequencing of the human genome by all worldwide efforts is roughly $3 \times 10^9/15$ years, or 550,000 bases/day, at a cost of >$1/base. Sequencing by the methods of the invention described herein will constitute an inordinate breakthrough in the rate of sequencing. The predicted time to complete one human genome with one machine is ~15 hours. Several dynamic arrays in parallel will be able to complete the sequence of one human genome in a fraction of an hour.

A method for sequencing a polymer of linked units is also encompassed by the invention. The method is performed by obtaining polymer dependent impulses from each of a plurality of overlapping polymers, at least a portion of each of the polymers having a sequence of linked units identical to the other of the polymers, and comparing the polymer dependent impulses to obtain a sequence of linked units which is identical in the plurality of polymers.

The plurality of overlapping polymers is a set of polymers in which each polymer has at least a portion of its sequence of linked units which is identical to the other polymers. The portion of sequence which is identical is referred to as the overlapping region and which includes at least ten contiguous units.

A "polymer" as used herein is a compound having a linear backbone of individual units which are linked together by linkages. In some cases the backbone of the polymer may be branched. Preferably the backbone is unbranched. The term "backbone" is given its usual meaning in the field of polymer chemistry. The polymers may be heterogeneous in backbone composition thereby containing any possible combination of polymer units linked together Such as peptidenucleic acids (which have amino acids linked to nucleic acids and have enhanced stability). In a preferred embodiment the polymers are homogeneous in backbone composition and are, for example, nucleic acids, polypeptides, polysaccharides, carbohydrates, polyurethanes, polycarbonates, polyureas, polyethyleneimines, polyarylene sulfides, polysiloxanes, polyimides, polyacetates, polyamides, polyesters, or polythioesters. In the most preferred embodiments, the polymer is a nucleic acid or a polypeptide. A "nucleic acid" as used herein is a biopolymer comprised of nucleotides, such as deoxyribose nucleic acid (DNA) or ribose nucleic acid (RNA). A polypeptide as used herein is a biopolymer comprised of linked amino acids.

As used herein with respect to linked units of a polymer, "linked" or "linkage" means two entities are bound to one another by any physicochemical means. Any linkage known to those of ordinary skill in the art, covalent or non-covalent, is embraced. Such linkages are well known to those of ordinary skill in the art. Natural linkages, which are those ordinarily found in nature connecting the individual units of a particular polymer, are most common. Natural linkages include, for instance, amide, ester and thioester linkages. The individual units of a polymer analyzed by the methods of the invention may be linked, however, by synthetic or modified linkages. Polymers where the units are linked by covalent bonds will be most common but also include hydrogen bonded, etc.

The polymer is made up of a plurality of individual units. An "individual unit" as used herein is a building block or monomer which can be linked directly or indirectly to other building blocks or monomers to form a polymer. The polymer preferably is a polymer of at least two different linked units. The at least two different linked units may produce or be labeled to produce different signals, as discussed in greater detail below. The particular type of unit will depend on the type of polymer. For instance DNA is a biopolymer composed of a deoxyribose phosphate backbone composed of units of purines and pyrimidines such as adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. RNA is a biopolymer comprised of a ribose phosphate backbone composed of units of purines and pyrimidines such as those described for DNA but wherein uracil is substituted for thymidine. The DNA nucleotides may be linked to one another by their 5' or 3' hydroxyl group thereby forming an ester linkage. The RNA nucleotides may be linked to one another by their 5', 3' or 2' hydroxyl group thereby forming an ester linkage. Alternatively, DNA or RNA units having a terminal 5', 3' or 2' amino group may be linked to the other units of the polymer by the amino group thereby forming an amide linkage.

Whenever a nucleic acid is represented by a sequence of letters it will be understood that the nucleotides are in 5'→3' order from left to right and that "A" denotes adenosine, "C" denotes cytidine, "G" denotes guanosine, "T" denotes thymidine, and "U" denotes uracil unless otherwise noted.

The polymers may be native or naturally-occurring polymers which occur in nature or non-naturally occurring polymers which do not exist in nature. The polymers typically include at least a portion of a naturally occurring polymer. The polymers can be isolated or synthesized de novo. For example, the polymers can be isolated from natural sources e.g. purified, as by cleavage and gel separation or may be synthesized e.g.,(i) amplified in vitro by, for example, polymerase chain reaction (PCR); (ii) synthesized by, for example, chemical synthesis; (iii) recombinantly produced by cloning, etc.

The polymer or at least one unit specific marker thereof is in a form which is capable of interacting with an agent or station to produce a signal (polymer dependent impulse) characteristic of that interaction. The unit specific marker of a polymer which is capable of undergoing such an interaction is said to be labeled. If a unit specific marker of a polymer can undergo that interaction to produce a characteristic signal, then the polymer is said to be intrinsically labeled. It is not necessary that an extrinsic label be added to the polymer. If a non-native molecule, however, must be attached to the individual unit specific marker of the polymer to generate the interaction producing the characteristic signal, then the polymer is said to be extrinsically labeled. The "label" may be, for example, light emitting, energy accepting, fluorescent, radioactive, or quenching.

Many naturally occurring units of a polymer are light emitting compounds or quenchers. For instance, nucleotides of native nucleic acid molecules have distinct absorption spectra, e.g., A, G, T, C, and U have absorption maximums at 259 nm, 252 nm, 267 nm, 271 nm, and 258 nm respectively. Modified units which include intrinsic labels may also be incorporated into polymers. A nucleic acid molecule may include, for example, any of the following modified nucleotide units which have the characteristic energy emission patterns of a light emitting compound or a quenching compound: 2,4-dithiouracil, 2,4-Diselenouracil, hypoxanthine, mercaptopurine, 2-aminopurine, and selenopurine.

A unit or unit specific marker may also be considered to be intrinsically labeled when a property of the unit specific marker other than a light emitting, quenching or radioactive property provides information about the identity of the unit specific marker without the addition of an extrinsic label. For instance the shape and charge of the unit specific marker provides information about the unit specific marker which can result in a specific characteristic signal, such as a change in conductance arising from the blockage of a conductance path by the unit.

The types of labels useful according to the methods of the invention, guidelines for selecting the appropriate labels, and methods for adding extrinsic labels to polymers are provided in more detail in co-pending PCT patent application PCT/US98/03024 and U.S. Ser. No. 09/134,411, which are incorporated by reference.

In addition to information about a specific unit the methods of the invention may be used to identify greater than one unit at a time in order to provide information about a polymer. As discussed herein the invention is useful for detecting polymer dependent impulses arising from unit specific markers, which encompass single units as well as multiple units. In one aspect the method is carried out by providing a labeled polymer of linked units, detecting signals from labeled unit specific markers of less than all of the linked units, and storing a signature of the signals detected to analyze the polymer. In this aspect of the invention each unit of the labeled polymer may be labeled with a unit specific marker or less than all of the units may be labeled with a unit specific marker.

This method is particularly useful for analyzing multiple units of a polymer at one time. This is accomplished by using a unit specific marker which is labeled and which interacts with more than one unit in a sequence specific manner. As used herein a "unit specific marker" is a compound which specifically interacts with one or more units of a polymer and is capable of identifying those units. For instance a unit specific marker for a nucleic acid molecule can be a labeled dimers, trimers, etc. which bind to a specific sequence of bases, such as TG, AG, ATC, etc. By identifying the presence or position of the labeled markers structural information about the polymer can be derived. For instance, the presence of the marker on a polymer can reveal the identity of the polymer. This enables the presence or absence of a polymer in a solution or mixture of polymers to be determined. The order, distance, number etc. of the markers on a polymer can provide information about the sequence or composition of a polymer. Other unit specific markers include but are not limited to sequence specific major and minor groove binders and intercallators, sequence specific DNA and peptide binding proteins, sequence specific peptide-nucleic acids, mass labels, fluorophores, antibodies or fragments thereof, restriction enzymes, probes, doubly tagged nucleotides, etc. Many such unit specific markers exist and are well known to those of skill in the art.

A "labeled unit specific marker" as used herein is any unit specific marker in a polymer that identifies a particular unit or units. A labeled unit specific marker includes, for instance, fluorescent markers which are bound to a particular unit or units, proteins, peptides, nucleic acids, polysaccharides, short oligomers, tRNA, etc. that recognize and bind to a particular unit or units and that can be detected by e.g., possessing an intrinsically labeled property or including an extrinsic label or by binding to another detection molecule such as an antibody.

This type of analysis can be used in one embodiment to identify DNA fragments by analyzing the hybridization patterns of multiple probes to individual fragments of polymers. The current state-of-the-art methods for hybridization analysis of DNA rely upon DNA chips. The methods of the invention are advantageous for a number of reasons. The number, type, order, and distance between the multiple probes bound to an unknown fragment of DNA can be determined. This information can be used to identify the number of differentially expressed genes unambiguously. Current hybridization approaches can only determine the type of probes bound to a given fragment. Furthermore, the methods of the invention are able to quantitate precisely the actual number of particular expressed genes. Current methods rely on quantitation of fluorescence intensities, which often give rise to errors due to non-linearities in the detection system. Given the great amount of information generated, the methods of the invention do not require a selection of expressed genes or unknown nucleic acids to be assayed. This is in contrast to the requirement of different DNA chips for different genes, sets of expressed genes to be analyzed, and also different organisms. The methods of the invention can identify the unknown expressed genes by computer analysis of the hybridization patterns generated. The data obtained from linear analysis of the DNA probes are then matched with information in a database to determine the identity of the target DNA. The methods can thus analyze information from hybridization reactions, which can then be applied to diagnostics and determination of gene expression patterns.

A "signature" as used herein is a sequence-specific signal arising from a labeled polymer. The signature includes information about the structure of the polymer. For instance, the signature of a polymer may be defined by a series of consecutive unit specific markers or by specific unit specific markers spaced a particular distance apart from one another. The signature of the polymer identifies the polymer. Signatures are useful for uniquely identifying fragments by identifying bases at certain positions along the length of a strand of DNA. The probability of knowing any one position is ¼. Unambiguous identification of a fragment comes with roughly twenty positions identified ($¼^{20}=9.1\times120^{-3}$). For a fragment with 20 detected labels and 10% detection/labeling, the size of the fragment needs to be only 200 base pairs. The proposed read length is on the order of kilobases, which should unambiguously identify any fragment. The identification of fragments allows for grouping by similar sequences, making sequence reconstruction by population analysis possible.

The data obtained from the polymer dependent impulses may be stored in a database, or in a data file, in the memory system of the computer. The data for each polymer may be stored in the memory system so that it is accessible by the processor independently of the data for other polymers, for example by assigning a unique identifier to each polymer.

The information contained in the data and how it is analyzed depends on the number and type of labeled unit specific markers that were caused to interact with the agent to generate signals. For instance if every unit specific marker of a single polymer, each type of unit specific marker (e.g., all the A's of a nucleic acid) having a specific type of label, is labeled then it will be possible to determine from analysis of a single polymer the order of every unit specific marker within the polymer. If, however, only one of the four types of units of a nucleic acid is labeled then more data will be required to determine the complete sequence of the nucleic acid. Additionally, the method of data analysis will vary depending on whether the polymer is single stranded or double stranded or otherwise complexed. Several labeling schemes and methods for analysis using the computer system data produced by those schemes are described in more detail below. The labeling strategies are described with respect to nucleic acids for ease of discussion. Each of these strategies, however, is useful for labeling all polymers.

Several different strategies of labeling are possible, involving permutations of different types of units labeled, different percentage of units labeled, and single-stranded or double-stranded labeling. Set forth below are examples of labeling strategies useful according to the invention. The invention is, however, not limited to the exemplary details provided below. The labeling methods described herein and data obtained from such methods are described with reference to DNA to simplify the discussion. The invention, however, is not limited to methods of analyzing DNA, but rather may be utilized with any type of polymer which is composed of individual monomeric units. It will be clear to those of ordinary skill in the art that when the description below refers to DNA or nucleic acids, any polymer many be substituted, and when the description refers to a nucleotide, a base or specifically A, C, T, or G, these terms may be substituted with the particular monomeric units of the desired polymer. For instance, the polymer may be a peptide, and in that case the monomeric units is an amino acid. The simplest labeling scheme involves the labeling of all four nucleotides with different labels. Labeling schemes in which three, two, or even one unit are labeled, or wherein various combinations of units are labeled using unit specific markers which span multiple nucleotides also possible.

A four nucleotide labeling scheme can be created where the A's, C's, G's, and T's of a target DNA is labeled with different labels. Such a molecule, if moved linearly past a station, will generate a linear order of signals which correspond to the linear sequence of nucleotides on the target DNA. The advantage of using a four nucleotide strategy is its ease of data interpretation and the fact that the entire sequence of unit specific markers can be determined from a single labeled polymer. Adding extrinsic labels to all four bases, however, may cause steric hindrance problems. In order to reduce this problem the intrinsic properties of some or all of the nucleotides may be used to label the nucleotides. As discussed above, nucleotides are intrinsically labeled because each of the purines and pyrimidines have distinct absorption spectra properties. In each of the labeling schemes described herein the nucleotides may be either extrinsically or intrinsically labeled but it is preferred that at least some of the nucleotides are intrinsically labeled when the four nucleotide labeling method is used. It is also preferred that when extrinsic labels are used with the four nucleotide labeling scheme that the labels be small and neutral in charge to reduce steric hindrance.

A three nucleotide labeling scheme in which three of the four nucleotides are labeled may also be performed. When only three of the four nucleotides are labeled analysis of the data generated by the methods of the invention is more complicated than when all four nucleotides are labeled. The data is more complicated because the number and position of the nucleotides of the fourth unlabeled type must be determined separately. One method for determining the number and position of the fourth nucleotide utilizes analysis of two different sets of labeled nucleic acid molecules. For instance, one nucleic acid molecule may be labeled with A, C, and G, and another with C, G, and T. Analysis of the linear order of labeled nucleotides from the two sets yields sequence data. The three nucleotides chosen for each set can have many different possibilities as long as the two sets contain all four labeled nucleotides. For example, the set ACG can be paired with a set of labeled CGT, ACT or AGT.

The sequence including the fourth nucleotide also may be determined by using only a single labeled polymer rather then a set of at least two differently labeled polymers using a negative labeling strategy to identify the position of the fourth nucleotide on the polymer. Negative labeling involves the identification of sequence information based on units which are not labeled. For instance, when three of the nucleotides of a nucleic acid molecule are labeled with a label which provides a single type of signal, the points along the polymer backbone which are not labeled must be due to the fourth nucleotide. This can be accomplished by determining the distance between labeled nucleotides on a nucleic acid molecule. For example A, C, and G are labeled and the detectable signals generated indicated that the nucleic acid molecule had a sequence of AGGCAAACG (SEQ. ID. No. 1). If the distances between each of the nucleotides in the nucleic acid molecule are equivalent to the known inter-nucleotide distance for a particular combination of nucleotides except the distance between G and G is twice the normal inter-nucleotide distance then a T is positioned between the two G's and the entire molecule has a sequence of AGTGCAAACG (SEQ. ID. No. 2). The distance between nucleotides can be determined in several ways. Firstly, the polymer and the station may be moved relative to one another in a linear manner and at a constant rate of speed such that a single unit specific marker of the nucleic acid molecule will pass the station at a single time interval. If two time intervals elapse between detectable signals then the unlabeled nucleotide which is not capable of producing a detectable signal is present within that position. This method of determining the distance between unit specific markers is discussed in more detail below in reference to random one base labeling. Alternatively the polymer and the station may be caused to interact with one another such that each unit specific marker interacts simultaneously with a station to produce simultaneous detectable signals. Each detectable signal generated occurs at the point along the polymer where the unit specific marker is positioned. The distance between the detectable signals can be calculated directly to determine whether an unlabeled unit specific marker is positioned anywhere along the nucleic acid molecule.

Nucleic acid molecules may also be labeled according to a two nucleotide labeling scheme. Six sets of two nucleotide labeled nucleic acid molecule can be used to resolve the data and interpret the nucleotide sequence. Ambrose et al., 1993 and Harding and Keller, 1992 have demonstrated the synthesis of large fluorescent DNA molecules with two of the nucleotides completely extrinsically labeled. The average size of the molecules were 7 kb. Six different combinations of two nucleotide labeling are possible using the following formula:

$$(_nC_k) = \frac{n!}{k!(n-k)!} = \frac{4}{2!2!} = 6$$

where n nucleotides are taken k at a time. The possible combinations are AC, AG, AT, CG, CT, and GT. Knowledge of the linear order of the labels in each of the sets allows for successful reconstruction of the nucleic acid sequence. Using a 4-mer (5'ACGT3) as a model sequence, the theory can be demonstrated. The first set, AC, gives the information that there must be a C after the A. This does not give information about the number of nucleotides intervening the A and the C nor does it give information about any G's or T's preceding the A. The second set, AG, shows that there is also a G after the A. Set AT shows there is a T after the A. From these three sets, it is then known that the target DNA is a 4-mer and that one C, one G, and one T follow the A. The subsequent sets give information on the ordering of these three nucleotides following the A. Set CG shows that G follows C. Set CT shows that T follows C. Set GT finishes the arrangement to give the final deciphered sequence of 5'ACGT3. In addition to the method using six labeled sets of nucleic acid molecules, the sequence can be established by combing information about the distance between labeled nucleotides generating detectable signals as described above and information obtained from fewer than six sets of two nucleotide labeled nucleic acid molecules.

A fourth labeling scheme, the random one nucleotide labeling scheme also may be used. In this method, distance information which is obtained by either population analysis and/or instantaneous rate of DNA movement is used to determine the number of nucleotides separating two labeled nucleotides. Analysis of four differently labeled target molecules yields the complete sequence.

One method of analysis with these labeling methods includes the use of complementary base information. FIG. 1 demonstrates the labeling strategy in which two differently labeled DNA samples are required. The first sample has two of its non-complementary bases randomly labeled with the same fluorophore. Non-complementary pairs of bases are AC, AG, TC, and TG. The second sample has one of its bases randomly labeled. The base chosen for the second sample can be any of the four bases. In the example given, the two non-complementary bases are chosen to be A and C. As a result, two samples are prepared, one with labeled A's and C's and another with labeled A's. The DNA can be, for example, genomically digested, end-labeled, purified, and analyzed by nanochannel FRET sequencing. The sequence-specific FRET information arising from each fragment is sorted into one of two complementary strand groups. Sorting allows population analysis to determine the positions of all the desired bases. The figure illustrates the generation of sequence information from the sorted data. The first group of analyzed information yields the positions of all the A's and C's on one strand. The second group analyzed yields knowledge of all the A's and C's on one strand. The same procedure is applied to the complementary stand. Knowledge of the complementary strand's A's and C's is identical to knowledge of the T's and G's on the other stand. The result is sequence reconstruction. To cross-verify the sequence, the process can be repeated for the other pairs of non-complementary bases such as TG, TC and AG.

There are two methods of determining the distance between bases. One requires determining the instantaneous rate of DNA movement, which is readily calculated from the duration of energy transfer or quenching for a particular label. Another involves analyzing a population of target DNA molecules and its corresponding Gaussian distance distributions.

Figure 2:
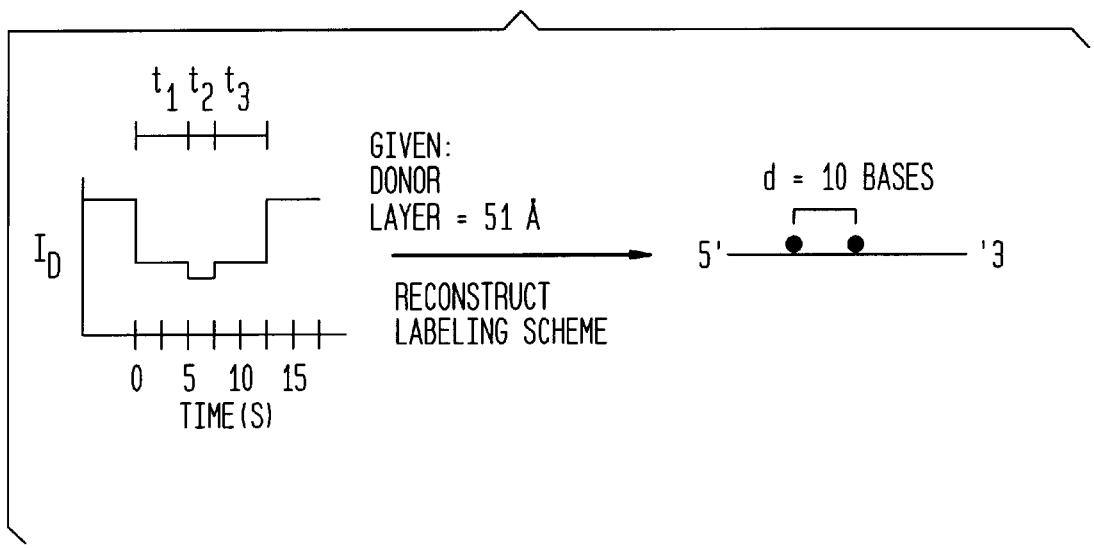
FIG. 2 is a graph of raw data demonstrating changes in energy emission patterns to determine distance information through the instantaneous rate method. The changes in energy patterns result from sequential detectable signals which when plotted produce a curve that from left to right shows two energy intensity decreases, followed by two energy intensity increases. The rate is 6.8 A/s and $t_1$ is the time between the entry of the first and second labels.

The instantaneous rate method, involves a determination of distance separation based on the known instantaneous rate of DNA movement (v) multiplied by the time of separation between signals (t). Instantaneous rate is found by measuring the time that it takes for a labeled nucleotide to pass by the interaction station. Since the length of the concentrated area of agent (d) is known (through calibration and physical measurement of the localized region of the agent, e.g., the thickness of a concentrated donor fluorophore area), the rate is simply $v=d/t$. As shown in FIG. 2 analysis of raw data demonstrating changes in energy emission patterns resulting from sequential detectable signals when plotted produces a curve which from left to right shows two energy intensity decreases, followed by two energy intensity increases. The plateau from the first energy intensity decrease (denoted $t_1$) is double that of the second plateau ($t_2$). The length of the interaction station is given as 51 Å. From this given information, the number of labeled nucleotides is known. Furthermore, the distance of separation of the two is determined by relating the rate of DNA movement to the time of the donor intensity plateaus.

The number of labeled nucleotides is simply denoted by the number of intensity decreases. In FIG. 2, there are two intensity decreases. Accordingly, there must be two detectable labels on the DNA. To determine the distance of base separation, it is necessary to know the instantaneous rate of DNA movement, which is found by knowing the time for one labeled nucleotide to cross the localized region of the agent and the length of the localized region of the agent. The length of the localized region of the agent is given as 51 Å. The time for one labeled nucleotides crossing the localized region of the agent is bounded by the first intensity decrease and the first intensity increase (denoted as the gray shaded region, 7.5 s). The rate of DNA movement is 6.8 Å/s. The base separation is derived from the time separating the labeled nucleotides ($t_1$=5 s) multiplied by the rate (6.8 Å), which is equal to 10 base pairs. As a means of cross-verification, 51 Å–$t_2$v also yields the base separation.

In the population method the entire population of labeled nucleotide is considered. Knowledge of the length of the localized region of the agent and instantaneous rate, as required for the rate method, is not necessary. Use of population analyses statistically eliminates the need for precision measurements on individual nucleic acid molecules.

An example of population analyses using five nucleic acid molecules each traversing a nanochannel is described below. Five molecules representing a population of identical DNA fragments are prepared. In a constant electric field, the time of detection between the first and second labeled nucleotide should be identical for all the DNA molecules. Under experimental conditions, these times differ slightly, leading to a Gaussian distribution of times. The peak of the Gaussian distribution is characteristic of the distance of separation (d) between two labeled nucleotides.

An additional example utilizing a population of one nucleotide randomly labeled nucleic acid molecule (six molecules represent the population) further illustrates the concept of population analysis and the determination of distance information. The nucleic acid is end-labeled to provide a reference point. With enough nucleic acid molecules, the distance between any two A's can be determined. Two molecules, when considered as a sub-population, convey the base separation molecules, distributions of 4 and 6 base separations are created. Extending the same logic to rest of the population, the positions of all the A's on the DNA can be determined. The entire sequence is generated by repeating the process for the other three bases (C, G, and T).

Figure 3:
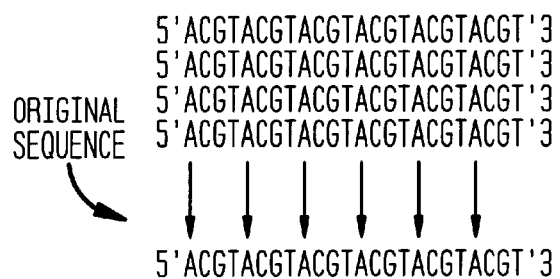
FIG. 3 shows a schematic of a random labeling method using a one nucleotide labeling scheme where less than all of the one nucleotide are labeled.

In addition to labeling all of one type of unit specific marker in the above-described examples, it is possible to use various labeling schemes where not every nucleotide of the nucleotides or markers to be labeled is labeled. An outline of a one nucleotide labeling scheme where less than all of the one nucleotide are labeled is shown in FIG. 3. A representative population of random A-labeled fragments for a 16-mer with the sequence 5'ACGTACGTACGTACGT3' (SEQ. ID. No. 3). Each individually labeled DNA molecule has half of its A's labeled in addition to 5' and 3' end labels. With a large population of randomly labeled fragments, the distance between every successive A on the target DNA can be found. The end labels serve to identify the distance between the ends of the DNA and the first A. Repeating the same analysis for the other nucleotides generates the sequence of the 16-mer by compiling the data to identify the position of all of the As within that population of nucleic acid molecules. These steps can then be repeated using unit specific markers for the other nucleotides in the population of nucleic acids. The advantages of using such a method includes lack of steric effects and ease of labeling. This type of labeling is referred to as random labeling. A polymer which is "randomly labeled" is one in which fewer than all of a particular type of unit specific marker are labeled. It is unknown which unit specific markers of a particular type of a randomly labeled polymer are labeled.

Figure 4:
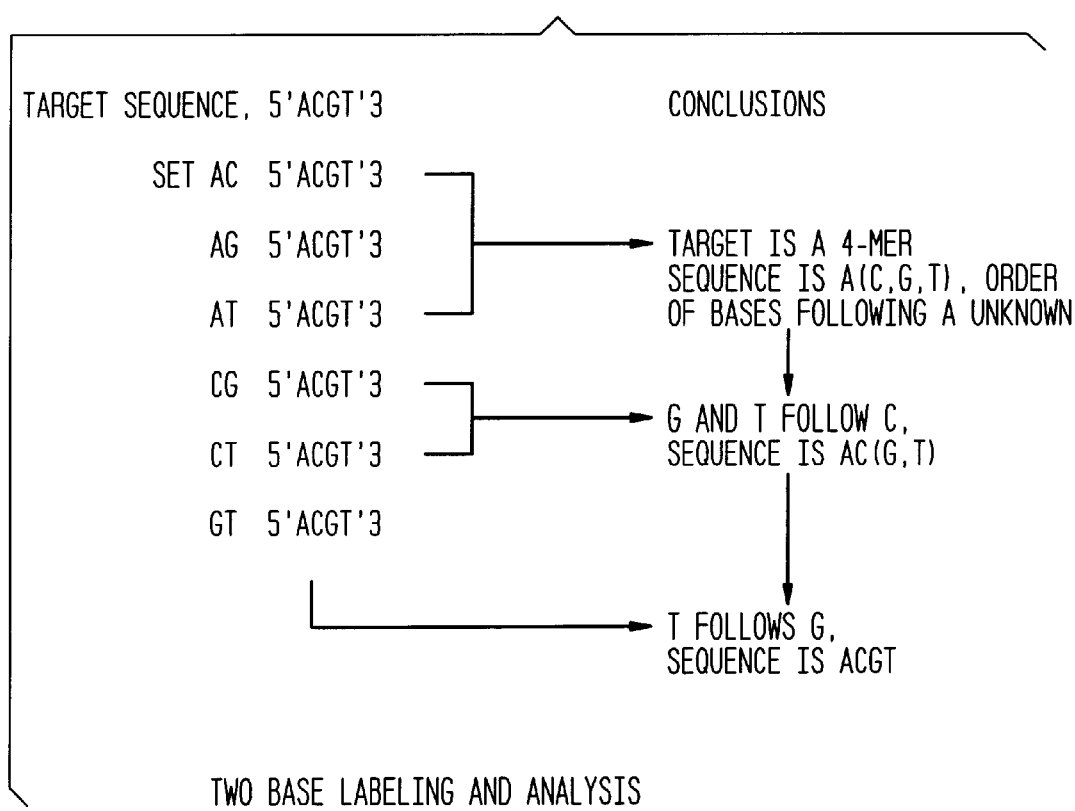
FIG. 4 shows a schematic of a random labeling method using a two nucleotide labeling scheme.

A similar type of analysis may be performed by labeling each of the four nucleotides incompletely but simultaneously within a population. For instance, each of the four nucleotides may be partially labeled with its own unit specific marker which gives rise to a different physical characteristic, such as color, size, etc. This can be accomplished to generate a data set containing information about all of the nucleotides from a single population analysis. For instance the method may be accomplished by partially labeling two nucleotide pairs at one time. Two nucleotide labeling is possible through the lowering of steric hindrance effects by using unit specific markers which recognize the two nucleotides of a nucleic acid strand and which contain a label such as a single fluorescent molecule. Ambrose et al., 1993 and Harding and Keller, 1992 have demonstrated that large fluorescent nucleic acid molecules with two of the nucleotides completely labeled are possible to achieve. The average size of the molecules studied were 7 KB. FIG. 4 demonstrates a two nucleotide labeling scheme. Partial labeling of three nucleotides is also possible. For instance, each of three nucleotides is partially labeled with a different unit specific marker. In this case, a population of single stranded nucleic acid molecules which are partially labeled with three specific nucleotide pair combinations is generated and can be analyzed.

Figure 5:
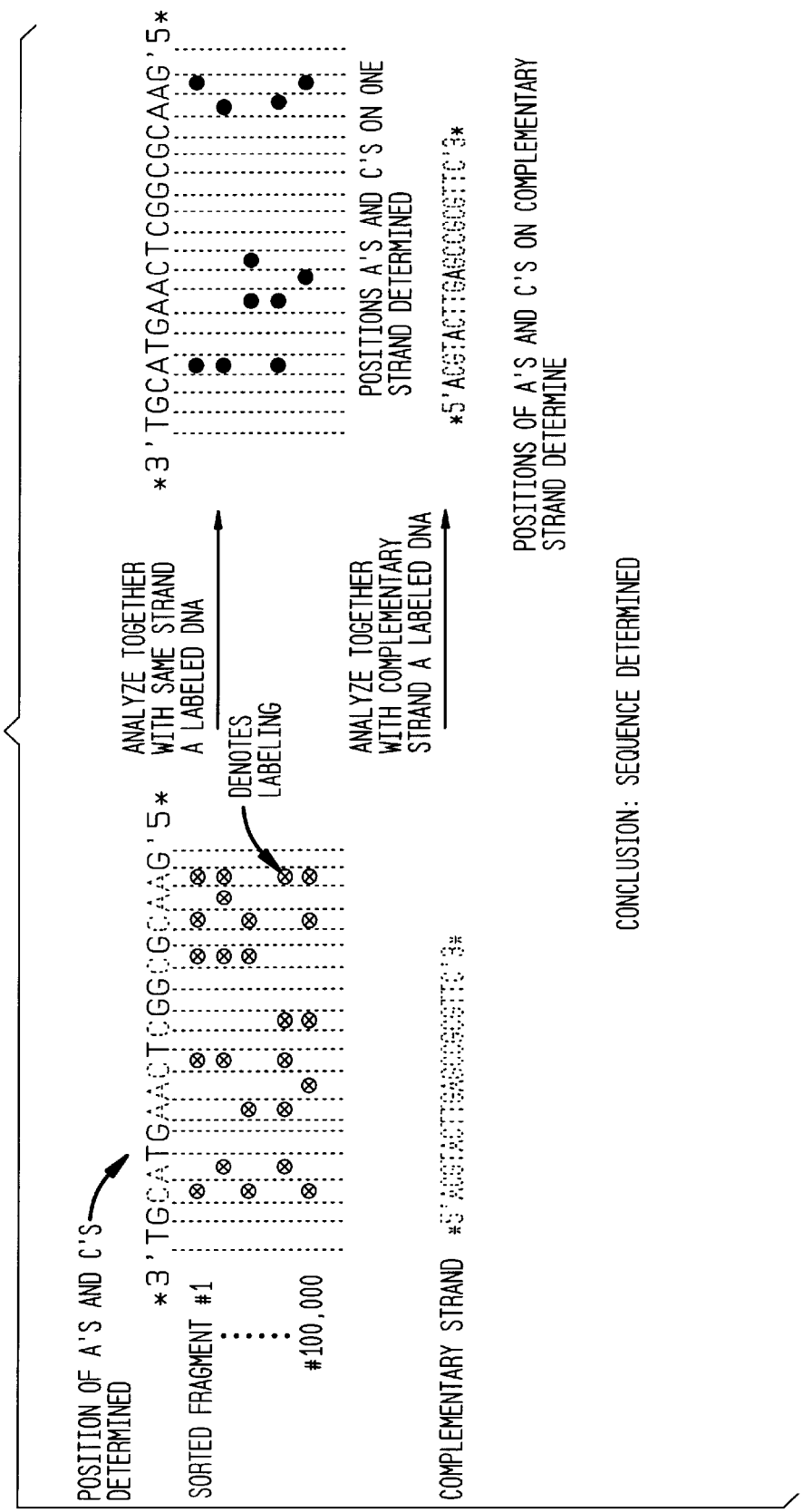
FIG. 5 shows a schematic of a random labeling method using two differently labeled nucleic acid samples.

The methods of the invention can also be achieved using a double stranded nucleic acid. In a double stranded nucleic acid, when a single nucleotide on two of the strands is labeled, information about two nucleotides becomes available for each of the strands. For instance, in the random and partial labeling of A's, knowledge about the A's and T's becomes available. FIG. 5 demonstrates a labeling strategy in which two differently labeled nucleic acid samples are prepared. The first sample has two non-complimentary nucleotides randomly labeled with the same fluorophore. Non-complimentary pairs of nucleotides are AC, AG, TC, and TG. The second sample has one of its nucleotides randomly labeled. The nucleotide chosen for the second sample may be any one of the four nucleotides. In the example provided, the two non-complimentary nucleotides are chosen to be A and C, and the single nucleotide is chosen to be A. Two samples are prepared, one with labeled A's and C's and another with labeled A's. The nucleic acid is genomically digested, end labeled, purified, and analyzed. Such procedures are well-known to those of ordinary skill in the art. The information from each fragment is sorted into one of two complimentary strand groups. Sorting the information allows the population analysis to determine the positions of all the desired nucleotides. FIG. 6 illustrates the generation of sequence information from the sorted data. The first group of data provides known positions of all the A's and C's on one strand. The second group of data provides known positions of all of the A's. The combination of these two data sets reveals the position of all of the A's and C's on one strand. The same procedure may be applied to the complimentary strand to determine the positions of the A's and C's on that strand. The resultant data reveals the entire sequence for both strands of the nucleic acid, based on the assumption that the strand includes the complimentary nucleotide pairs of A and C (A:T and C:G). To cross-verify the sequence, the process can be repeated for the other pairs of non-complimentary nucleotides such as TG, TC and AG.

A single-stranded two-nucleotide labeling scheme also can be performed on double stranded DNA when two of the nucleotides on one strand of DNA are fully replaced by labeled nucleotides. To reduce the steric constraints imposed by two extrinsically labeled nucleotides while preserving the theory behind two-nucleotide labeling, it is possible to label one nucleotide fully on each of the complementary strands to achieve the same end. This method involves using double-stranded DNA in which each strand is labeled with a different label. Six differently labeled duplex DNA sets will produce a data set which is adequate to provide sequence information. Each complementary strand of DNA should have one of the nucleotides labeled. In each of the duplex DNA sets, the equivalent of two different nucleotides (possible combinations are AC, AG, AT, CG, CT, GT) are labeled. When both complementary strands have the adenines labeled, this is equivalent to the combination AT. In duplex two-nucleotide labeling, the advantage is that only one nucleotide on each strand is labeled, allowing longer labeled strands to be synthesized as compared to two-nucleotide labeling on single-stranded DNA. In practice, it has been shown that synthesis of DNA fragments with one nucleotide completely labeled can be achieved with lengths much greater than 10 kb (Ambrose et al., 1993; Harding and Keller, 1992).

Figure 7:
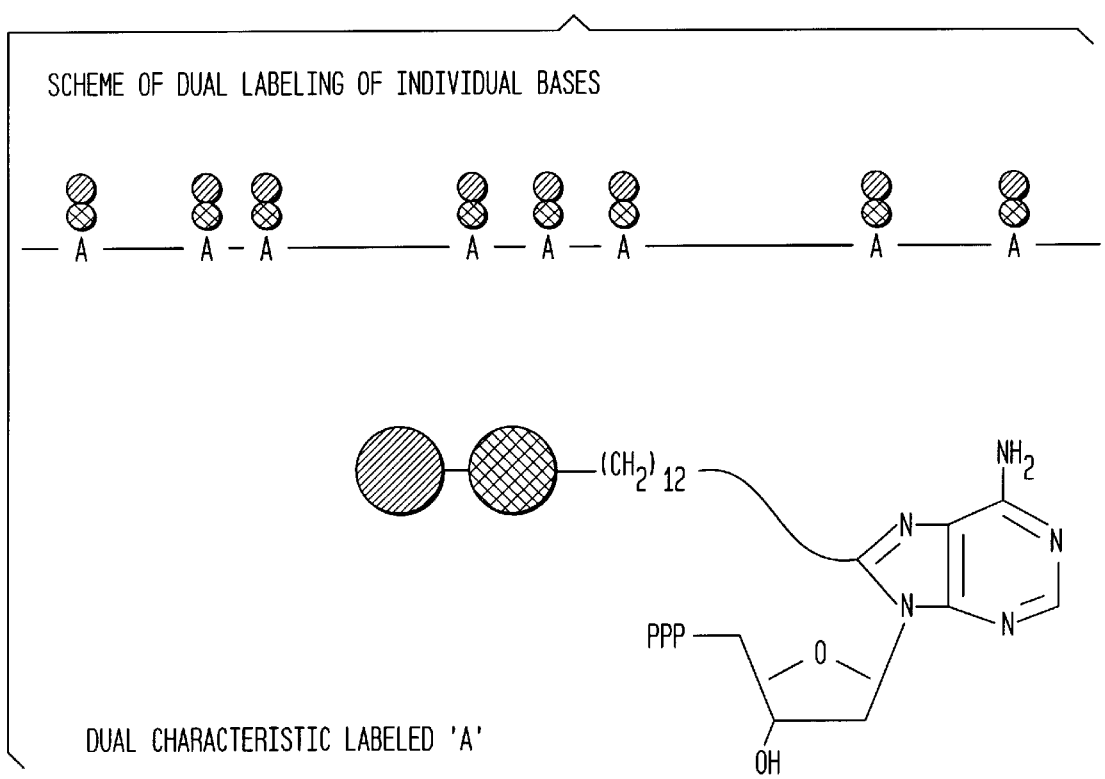
FIG. 7 illustrates the labeling of unit specific markers with more than one type of label.

By including more than one physical characteristic into the label, the simultaneous and overlapping reading of the nucleic acid within the same temporal frame may provide more accurate and rapid information about the positions of the labeled nucleotides than when only a single physical characteristic is included. label with different wavelength fluorophores. For instance, as demonstrated in FIG. 7, each of the nucleotides can include a double or triple Each of the fluorophores can be detected separately to provide distinct readings form the same sample.

In addition to the various combinations of single nucleotide labeling methods, two or more adjacent nucleotides may be specifically labeled. As described above a unit specific marker includes markers which are specific for individual nucleotides as well as markers which are specific for multiple nucleotides. Multiple nucleotides include two or more nucleotides which may or may not be adjacent. For instance if a unit specific marker is a complex of protein, the complex of proteins may interact with specific nucleotides that are adjacent to one another or which are separated by random nucleotides. This type of analysis is particularly useful because detection of the signal requires less resolution than with single nucleotide analysis. The more complex the analysis, the greater resolution of the system. Resolution as used herein refers to the number of nucleotides which can be resolved by the appropriate signal detection method used.

The signal detection method is described in more detail below. Preferably it includes methods such as nanochannel analysis, near-field scanning microscopy, atomic force microscopy, scanning electron microscopy, waveguide structures, etc.

The greater the number of nucleotides a unit specific marker spans and recognizes, the more amenable that unit specific marker is to low resolution means of detection. For any given number of nucleotide-spanning markers, the number of different unit specific markers which can be used is defined by the formula $4^n$, where n is the number of nucleotides detected by the unit specific marker. A unit specific marker which spans two nucleotides would be specific for one of 16 combinations of nucleotide pairs. These include, AC, AG, AT, AA, CC, CA, CG, CT, GA, GG, GC, GT, TA, TC, TG, and TT. A unit specific marker which spans three nucleotides would be specific for one of a combination of 64 three nucleotide pairs combinations. More than three nucleotide pairs combinations may also be used, and the number would increase according to the above formula. Using these types of unit specific markers, nucleotide sequence information can be reconstructed through a number of different means. The information generated from the reconstruction of the unit specific markers is not limited to the generation of sequence information, but additionally can be used to unambiguously identify fragments, provide the specific number of that combination of nucleotides found within the sequence, etc.

Various combinations of triplet unit specific markers bound to a nucleic acid molecule can be deciphered and analyzed using these methods. Without knowing the precise location of the triplet unit specific markers on the nucleic acid, the specificity given to a bound nucleic acid fragment is given as $N/4^n$ where N is the number of nucleotides in the fragment of target nucleic acid and n is the number of bound sites on the nucleic acid. The longer the strand of nucleic acid, the lower the specificity of the particular system. The specificity of the bound unit specific markers can be increased by determining the precise location of the triplet unit specific markers. In this case, the specificity is increased to $1/4^n$ which is the same as if an N-mer were bound to the target strand of nucleic acid.

Figure 8:
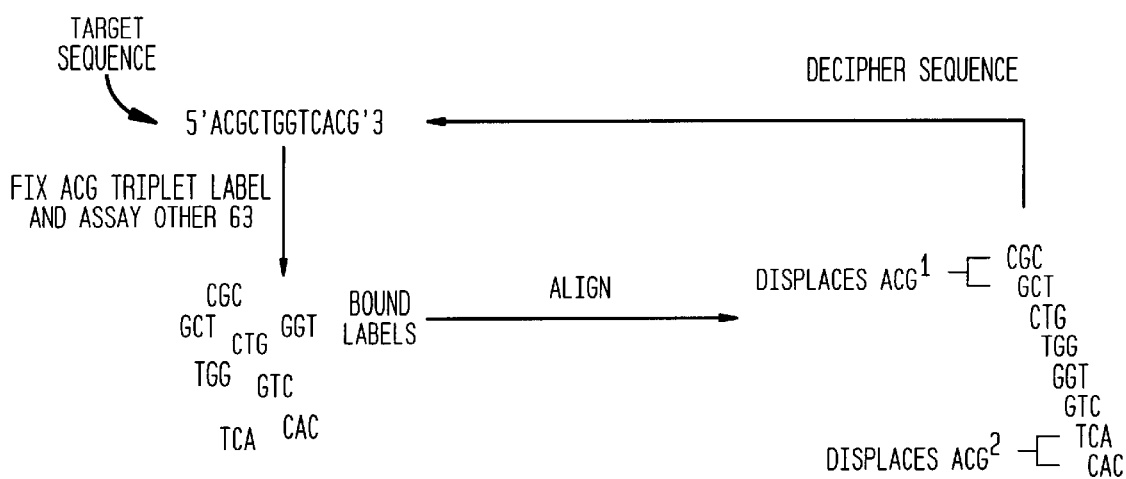
FIG. 8 shows a schematic of a random labeling method using triplet unit specific markers one of which is kept constant during the analysis.

The simplest method to determine the sequence of the nucleic acid molecule from the set of triplet unit specific markers is to examine two triplet 1 unit specific markers one time until all 64 unit specific markers are examined. If one of the triplet unit specific markers is kept constant during the analysis, the analysis is simplified. An example of this type of analysis is presented in FIG. 8. In the example, a short stretch of nucleic acid is analyzed using two triplet unit specific markers. The triplet unit specific markers are CGX and GXX. Using these markers, the two based positions after the first ACG triplet can be determined. Using the 63 different triplets together with the initial fragment ACG, information about flanking nucleotides and the contiguous sequence of the intervening nucleotides between the ACGs can be determined.

Using these methods of sequence analysis, problems which occur in other types of hybridization, etc. analysis are avoided. For instance, repeated sequences such as the Alu repeats in the human genome create analysis problems using hybridization sequencing methods. Such problems are avoided using the methods described herein. Using the methods described herein the number of repeats can be simply counted by the different triplets bound in each of the states. Hybridization sequencing analysis does not allow the determination of linear order or number of probes found between two probe sequences. The linear order and the precise quantitation of the number of probes bound allows an additional order of information which bypasses the difficulties faced in sequencing by hybridization. The methods of the invention are thus rapid and straightforward.

The method using triplet, etc. unit specific markers does not need to be performed sequentially. For instance, several triplets may be assayed simultaneously to provide an even more rapid method of analysis. The only limitation in simultaneous analysis is that none of the triplet unit specific markers used simultaneously should overlap one another. Therefore, the choice of one particular triplet sequence precludes the simultaneous use of triplet sequences which would overlap with that sequence. For example if the triplet sequence ACG is selected for analysis, 4 of the 64 sets of triplets may not be used during simultaneous analysis with this triplet. These include XXA, XAC, GXX, and CGX. Mathematically, the maximum number of fragments which a triplet label can preclude simultaneous probing with is determined by the following equation:

$$2[\Sigma 4^2 + 4^1] \text{ or generally } 2[\Sigma 4^{n-1} + 4^{n-2} \ldots 4^1]$$

where n is the number of nucleotides spanned by the labels. The sum is that a maximum of 40 fragments are precluded from simultaneous assay with the originally selected ACG triplet. Therefore, a total of 24 different fragments may be assayed at one time.

Figure 9:
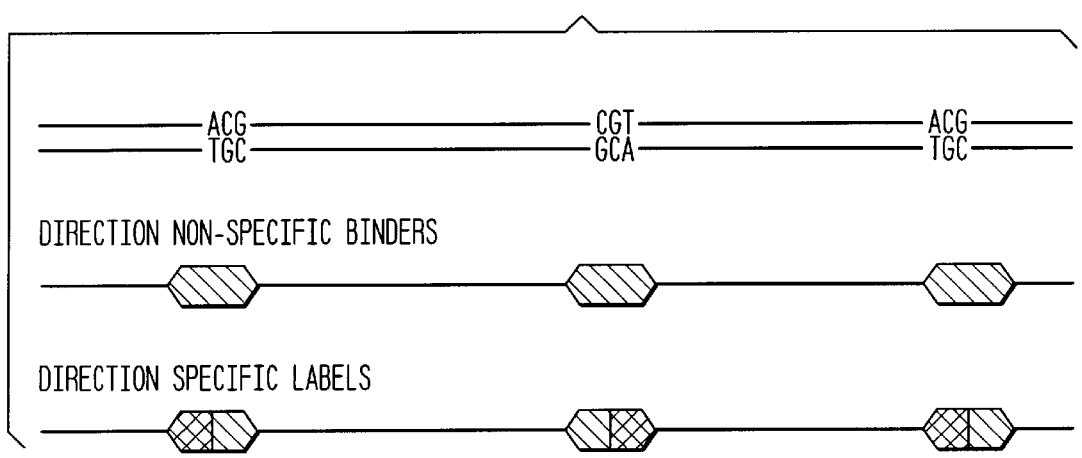
FIG. 9 shows a schematic of a random labeling method of a double stranded nucleic acid analysis using direction specific labels.
Figure 10:
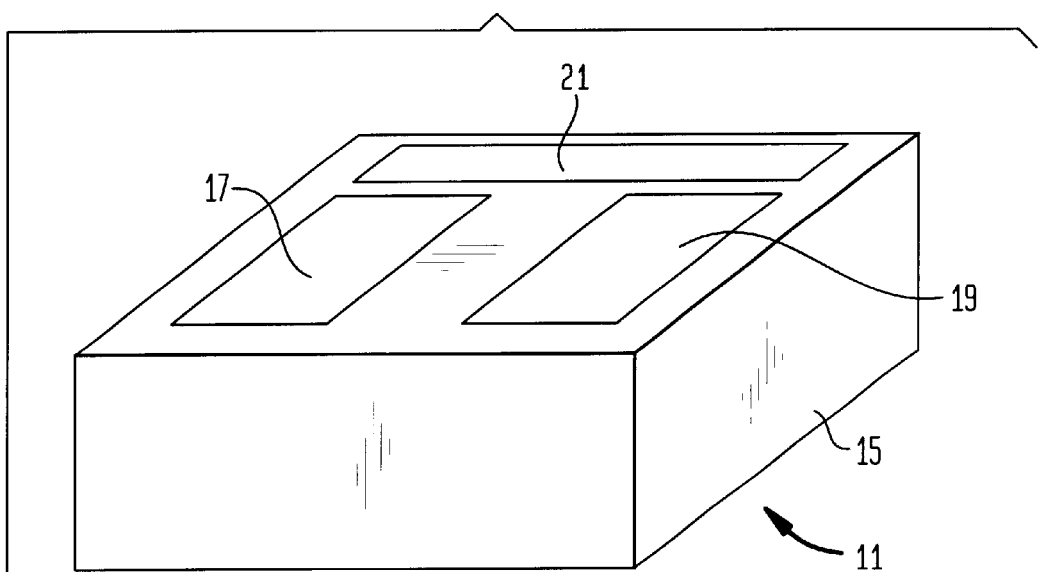
FIG. 10 is a sample kit according to the invention.
Figure 10:
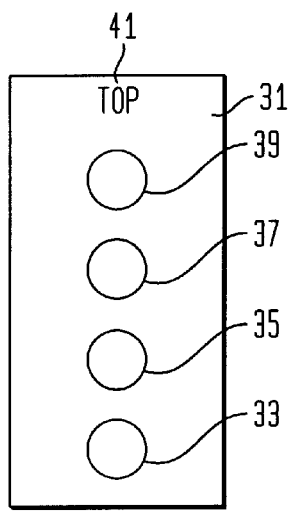
Figure 11B:
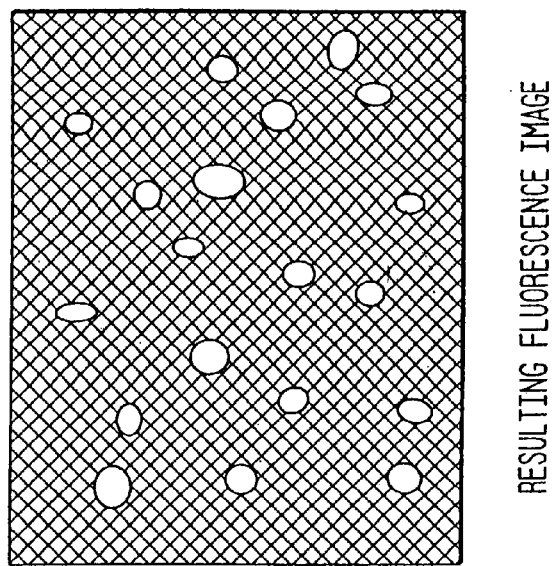
FIG. 11A is a schematic representation of a labeled DNA molecule moving through a nanochannel plate and 11B is a fluorescence illumination graph from which intensity can be determined.
Figure 11A:
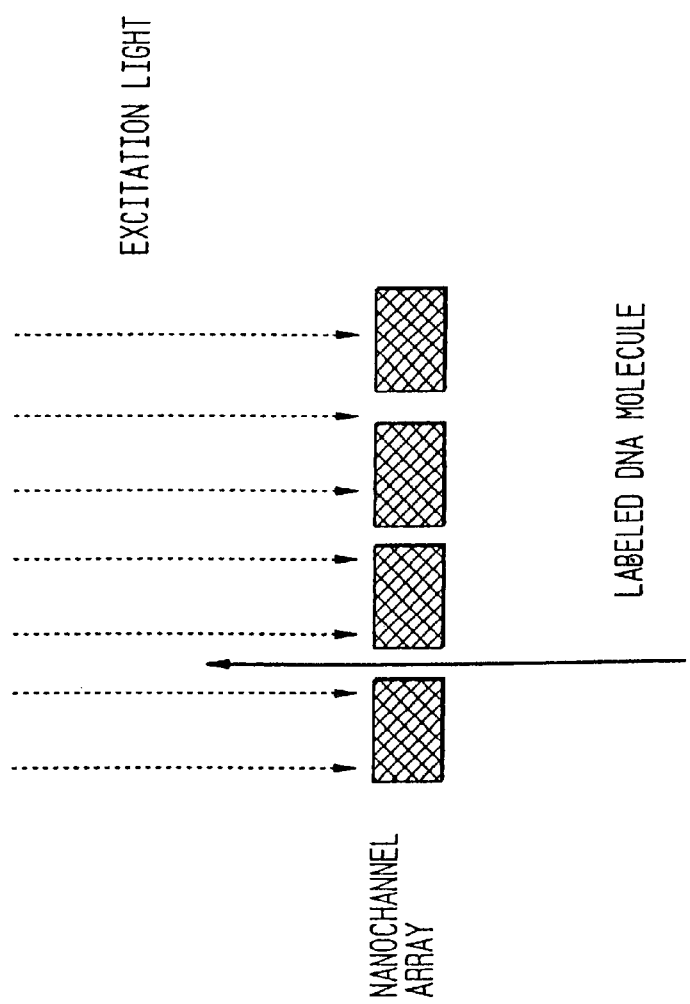

Double stranded nucleic acid analysis also may be accomplished using direction specific labels such as those shown in FIG. 9. Direction specific labels allow for discrimination between a combination of nucleotides such as ACG triplet on either strand. In the case of direction specific labels, the reversal of the center bound label shows that it is a label bound on the opposite strand. The labels have 5' to 3' or 3' to 5' directionality.

One use for the methods of the invention is to determine the sequence of units within a polymer. Identifying the sequence of units of a polymer, such as a nucleic acid, is an important step in understanding the function of the polymer and determining the role of the polymer in a physiological environment such as a cell or tissue. The sequencing methods currently in use are slow and cumbersome. The methods of the invention are much quicker and generate significantly more sequence data in a very short period of time.

The analysis methods described herein may be linear or non linear. The methods for generating sequence information based on data obtained from partially labeled polymers can be applied to data obtained by any method that produces polymer dependent impulses. The reconstruction of the sequence of the polymer from this type of data is an integral aspect of the invention. As long as the data is obtained by a method for detecting the polymer dependent impulses, whether it is obtained in a linear manner or not, the data may be analyzed according to the methods of the invention.

The signals may be detected sequentially or simultaneously. As used herein signals are detected "sequentially" when signals from different unit specific markers of a single polymer are detected spaced apart in time. Not all unit specific markers need to be detected or need to generate a signal to detect signals "sequentially." When the unit specific markers are sequentially exposed to the station the unit specific marker and the station move relative to one another. As used herein the phrase "the unit specific marker and the station move relative to one another" means that either the unit specific marker and the station are both moving or only one of the two is moving and the other remains stationary at least during the period of time of the interaction between the unit specific marker and the station. The unit specific marker and the station may be moved relative to one another by any mechanism. For instance the station may remain stationary and the polymer may be drawn past the station by an electric current. Other methods for moving the polymer include but are not limited to movement resulting from a magnetic field, a mechanical force, a flowing liquid medium, a pressure system, a gravitational force, and a molecular motor such as e.g., a DNA polymerase or a helicase when the polymer is DNA or e.g., myosin when the polymer is a peptide such as actin. The movement of the polymer may be assisted by the use of a channel, groove or ring to guide the polymer. Alternatively the station may be moved and the polymer may remain stationary. For instance the station may be held within a scanning tip that is guided along the length of the polymer.

In another embodiment signals are detected simultaneously. As used herein signals are "detected simultaneously" by causing a plurality of the labeled unit specific markers of a polymer to be exposed to a station at once. The plurality of the unit specific markers can be exposed to a station at one time by using multiple interaction sites. Signals can be detected at each of these sites simultaneously. For instance multiple stations may be localized at specific locations in space which correspond to the unit specific markers of the polymer. When the polymer is brought within interactive proximity of the multiple stations signals will be generated simultaneously. This may be embodied, for example, in a linear array of stations positioned at substantially equivalent distances which are equal to the distance between the unit specific markers. The polymer may be positioned with respect to the station such that each unit specific marker is in interactive proximity to a station to produce simultaneous signals.

Multiple polymers can be analyzed simultaneously by causing more than one polymer to move relative to respective stations at one time. The polymers may be similar or distinct. If the polymers are similar, the same or different unit specific markers may be detected simultaneously.

A preferred method for moving a polymer past a station according to the invention utilizes an electric field. An electric field can be used to pull a polymer through a channel because the polymer becomes stretched and aligned in the direction of the applied field as has previously been demonstrated in several studies (Bustamante, 1991; Gurrieri et al., 1990; Matsumoto et al., 1981).

Another method for moving a polymer past a station involves the use of a molecular motor. A molecular motor is a device which physically interacts with the polymer and pulls the polymer past the station. Molecular motors include but are not limited to DNA and RNA polymerases and helicases. DNA polymerases have been demonstrated to function as efficient molecular motors. Preferably the internal diameters of the regions of the polymerase which clamp onto the DNA is similar to that of double stranded DNA. Furthermore, large amounts of DNA can be able to be threaded through the clamp in a linear fashion. Molecular motors are described in more detail in co-pending U.S. provisional patent application 60/096,540, filed Aug. 13, 1998 and the U.S. patent application claiming priority thereto, the entire contents of which is hereby incorporated by reference.

The overall structure of the β-subunit of DNA polymerase III holoenzyme is 80 Å in diameter with an internal diameter of ~35 Å. In comparison, a full turn of duplex B-form DNA is ~34 Å. The beta subunit fits around the DNA, in a mechanism referred to as a sliding clamp mechanism, to mediate the processive motion of the holoenzyme during DNA replication. It is well understood that the β-subunit encircles DNA during replication to confer processivity to the holoenzyme (Bloom et al., 1996; Fu et al., 1996; Griep, 1995; Herendeen and Kelly, 1996; Naktinis et al., 1996; Paz-Elizur et al., 1996, Skaliter et al., 1996). Because the sliding clamp is the mechanism of processivity for a polymerase, it necessarily means that large amounts of DNA are threaded through the clamp in a linear fashion. Several kilobases are threaded through the clamp at one time (Kornberg and Baker, 1991).

The detectable signal (polymer dependent impulse) is produced at a station. A "station" as used herein is a region where a portion of the polymer to be detected, e.g. the unit specific marker, is exposed to, in order to produce a signal or polymer dependent impulse. The station may be composed of any material including a gas. Preferably the station is a non-liquid material. "Non-liquid" has its ordinary meaning in the art. A liquid is a non-solid, non-gaseous material characterized by free movement of its constituent molecules among themselves but without the tendency to separate. In another preferred embodiment the station is a solid material. In one embodiment when the interaction between the unit specific marker and the station produces a polymer dependent impulse the station is a signal generation station. One type of signal generation station is an interaction station. As used herein an "interaction station or site" is a region where a unit specific marker of the polymer interacts with an agent and is positioned with respect to the agent in close enough proximity whereby they can interact. The interaction station for fluorophores, for example, is that region where they are close enough so that they energetically interact to produce a signal.

The interaction station in one embodiment is a region of a nanochannel where a localized agent, such as an acceptor fluorophore, attached to the wall forming the channel, can interact with a polymer passing through the channel. The point where the polymer passes the localized region of agent is the interaction station. As each labeled unit specific marker of the polymer passes by the agent a detectable signal is generated. The agent may be localized within the region of the channel in a variety of ways. For instance the agent may be embedded in the material that forms the wall of the channel or the agent may be attached to the surface of the wall material. Alternatively the agent may be a light source which is positioned a distance from the channel but which is capable of transporting light directly to a region of the channel through a waveguide. An apparatus may also be used in which multiple polymers are transported through multiple channels. These and other related embodiments of the invention are discussed in more detail below. The movement of the polymer may be assisted by the use of a groove or ring to guide the polymer.

Other arrangements for creating interaction stations are embraced by the invention. For example, a polymer can be passed through a molecular motor tethered to the surface of a wall or embedded in a wall, thereby bringing unit specific markers of the polymer sequentially to a specific location, preferably in interactive proximity to a proximate agent, thereby defining an interaction station. A molecular motor is a biological compound such as polymerase, helicase, or actin which interacts with the polymer and is transported along the length of the polymer past each unit specific marker. Likewise, the polymer can be held from movement and a reader can be moved along the polymer, the reader having attached to it the agent. For instance the agent may be held within a scanning tip that is guided along the length of the polymer. Interaction stations then are created as the agent is moved into interactive proximity to each unit specific marker of the polymer.

The agent that interacts with the unit specific marker of the polymer at the interaction station is selected from the group consisting of electromagnetic radiation, a quenching source, and at fluorescence excitation source. "Electromagnetic radiation" as used herein is energy produced by electromagnetic waves. Electromagnetic radiation may be in the form of a direct light source or it may be emitted by a light emissive compound such as a donor fluorophore. "Light" as used herein includes electromagnetic energy of any wavelength including visible, infrared and ultraviolet.

As used herein, a quenching source is any entity which alters or is capable of altering a property of a light emitting source. The property which is altered can include intensity fluorescence lifetime, spectra, fluorescence, or phosphorescence.

A fluorescence excitation source as used herein is any entity capable of fluorescing or giving rise to photonic emissions (i.e. electromagnetic radiation, directed electric field, temperature, fluorescence, radiation, scintillation, physical contact, or mechanical disruption.) For instance, when the unit specific marker is labeled with a radioactive compound the radioactive emission causes molecular excitation of an agent that is a scintillation layer which results in fluorescence.

When a unit specific marker of the polymer is exposed to the agent the interaction between the two produces a signal. The signal provides information about the polymer. For instance if all unit specific markers of a particular type, e.g., all of the alanines, of a protein polymer are labeled (intrinsic or extrinsic) with a particular light emissive compound then when a signal characteristic of that light emissive compound is detected upon interaction with the agent the signal signifies that an alanine residue is present at that particular location on the polymer. If each type of unit specific marker e.g., each type of amino acid is labeled with a different light emissive compound having a distinct light emissive pattern then each amino acid will interact with the agent to produce a distinct signal. By determining what each signal for each unit specific marker of the polymer is, the sequence of units can be determined.

The interaction between the unit specific marker and the agent can take a variety of forms, but does not require that the unit specific marker and the agent physically contact one another. Examples of interactions are as follows. A first type of interaction involves the agent being electromagnetic radiation and the unit specific marker of the polymer being a light emissive compound (either intrinsically or extrinsically labeled with a light emissive compound). When the light emissive unit specific marker is contacted with electromagnetic radiation (such as by a laser beam of a suitable wavelength or electromagnetic radiation emitted from a donor fluorophore), the electromagnetic radiation causes the light emissive compound to emit electromagnetic radiation of a specific wavelength. The signal is then measured. The signal exhibits a characteristic pattern of light emission and thus indicates that a particular labeled unit specific marker of the polymer is present. In this case the unit specific marker of the polymer is said to "detectably affect the emission of the electromagnetic radiation from the light emissive compound."

A second type of interaction involves the agent being a fluorescence excitation source and the unit specific marker of the polymer being a light emissive or a radioactive compound. When the light emissive unit specific marker is contacted with the fluorescence excitation source, the fluorescence excitation source causes the light emissive compound to emit electromagnetic radiation of a specific wavelength. When the radioactive unit specific marker is contacted with the fluorescence excitation source, the nuclear radiation emitted from the unit specific marker causes the fluorescence excitation source to emit electromagnetic radiation of a specific wavelength. The signal then is measured.

A variation of these types of interaction involves the presence of a third element of the interaction, a proximate compound which is involved in generating the signal. For example, a unit specific marker may be labeled with a light emissive compound which is a donor fluorophore and a proximate compound can be an acceptor fluorophore. If the light emissive compound is placed in an excited state and brought proximate to the acceptor fluorophore, then energy transfer will occur between the donor and acceptor, generating a signal which can be detected as a measure of the presence of the unit specific marker which is light emissive. The light emissive compound can be placed in the "excited" state by exposing it to light (such as a laser beam) or by exposing it to a fluorescence excitation source.

Another interaction involves a proximate compound which is a quenching source. In this instance, the light emissive unit specific marker is caused to emit electromagnetic radiation by exposing it to light. If the light emissive compound is placed in proximity to a quenching source, then the signal from the light emissive unit specific marker will be altered.

A set of interactions parallel to those described above can be created wherein, however, the light emissive compound is the proximate compound and the unit specific marker is either a quenching source or an acceptor source. In these instances the agent is electromagnetic radiation emitted by the proximate compound, and the signal is generated, characteristic of the interaction between the unit specific marker and such radiation, by bringing the unit specific marker in interactive proximity with the proximate compound.

The mechanisms by which each of these interactions produces a detectable signal is known in the art. For exemplary purposes the mechanism by which a donor and acceptor fluorophore interact according to the invention to produce a detectable signal including practical limitations which are known to result from this type of interaction and methods of reducing or eliminating such limitations is set forth below.

Another preferred method of analysis of the invention involves the use of radioactively labeled polymers. The type of radioactive emission influences the type of detection device used. In general, there are three different types of nuclear emission including alpha, beta, and gamma radiation. Alpha emission cause extensive ionization in matter and permit individual counting by ionization chambers and proportional counters, but more interestingly, alpha emission interacting with matter may also cause molecular excitation, which can result in fluorescence. The fluorescence is referred to as scintillation. Beta decay which is weaker than alpha decay can be amplified to generate an adequate signal. Gamma radiation arises from internal conversion of excitation energy. Scintillation counting of gamma rays is efficient and produces a strong signal. Sodium iodide crystals fluoresce with incident gamma radiation.

A "scintillation" layer or material as used herein is any type of material which fluoresces or emits light in response to excitation by nuclear radiation. Scintillation materials are well known in the art. Aromatic hydrocarbons which have resonance structures are excellent scintillator. Anthracene and stilbene fall into the category of such compounds. Inorganic crystals are also known to fluoresce. In order for these compounds to luminesce, the inorganic crystals must have small amounts of impurities, which create energy levels between valence and conduction bands. Excitation and de-excitation can therefore occur. In many cases, the de-excitation can occur through phosphorescent photon emission, leading to a long lifetime of detection. Some common scintillator include NaI (Tl), ZnS (Ag), anthracene, stilbene, and plastic phosphors.

Many methods of measuring nuclear radiation are known in the art and include devices such as cloud and bubble chamber devices, constant current ion chambers, pulse counters, gas counters (i.e., Geiger-Müller counters), solid state detectors (surface barrier detectors, lithium-drifted detectors, intrinsic germanium detectors), scintillation counters, Cerenkov detectors, etc.

Analysis of the radiolabeled polymers is identical to other means of generating polymer dependent impulses. For example, a sample with radiolabeled A's can be analyzed by the system to determine relative spacing of A's on a sample DNA. The time between detection of radiation signals is characteristic of the polymer analyzed. Analysis of four populations of labeled DNA (A's, C's, G's, T's) can yield the sequence of the polymer analyzed. The sequence of DNA can also be analyzed with a more complex scheme including analysis of a combination of dual labeled DNA and singly labeled DNA. Analysis of a and C labeled fragment followed by analysis of an A labeled version of the same fragment yields knowledge of the positions of the A's and C's. The sequence is known if the procedure is repeated for the complementary strand. The system can further be used for analysis of polymer (polypeptide, RNA, carbohydrates, etc.), size, concentration, type, identity, presence, sequence and number.

The methods described above can be performed on a single polymer or on more than one polymer in order to determine structural information about the polymer.

In another preferred embodiment the signal generated by the interaction between the unit specific marker and the agent results from fluorescence resonance energy transfer (FRET) between fluorophores. Either the unit specific marker or the proximate compound/agent may be labeled with either the donor or acceptor fluorophore. FRET is the transfer of photonic energy between fluorophores. FRET has promise as a tool in characterizing molecular detail because of its ability to measure distances between two points separated by 10 Å to 100 Å. The angstrom resolution of FRET has been used in many studies of molecular dynamics and biophysical phenomena (for reviews see Clegg, 1995; Clegg, 1992; Selvin, 1995; and Wu and Brand, 1994). The resolving power of FRET arises because energy transfer between donor and acceptor fluorophores is dependent on the inverse sixth power of the distance between the probes. In practice, this resolution is about an order of magnitude better than that of the highest resolution electron microscope.

In order to undergo FRET, the emission spectrum of the donor overlaps with the excitation spectrum of the acceptor. The unit specific marker of the polymer is specifically labeled with an acceptor fluorophore. The agent is a donor fluorophore. A laser is tuned to the excitation wavelength of the donor fluorophore. As the polymer is moved through the channel, the donor fluorophore emits its characteristic wavelength. As the acceptor fluorophore moves into interactive proximity with the donor fluorophore, the acceptor fluorophore is excited by the energy from the donor fluorophore. The consequence of this interaction is that the emission of the donor fluorophore is quenched and that of the acceptor fluorophore is enhanced.

In order to generate an optimal efficient FRET signal for detection, two conditions should be satisfied. The first condition is efficient donor emission in the absence or acceptors. The second is efficient generation of a change in either donor or acceptor emissions during FRET. Each of these are described in more detail in co-pending PCT Patent Application PCT/US98/03024 and U.S. Ser. No. 09/134,411

A "detectable signal" as used herein is any type of signal or polymer dependent impulse which can be sensed by conventional technology. The signal produced depends on the type of station as well as the unit specific marker and the proximate compound if present. In one embodiment the signal is electromagnetic radiation resulting from light emission by a labeled (intrinsic or extrinsic) unit specific marker of the polymer or by the proximate compound. In another embodiment the signal is fluorescence resulting from an interaction of a radioactive emission with a scintillation layer. The detected signals may be stored in a database for analysis. One method for analyzing the stored signals is by comparing the stored signals to a pattern of signals from another polymer to determine the relatedness of the two polymers. Another method for analysis of the detected signals is by comparing the detected signals to a known pattern of signals characteristic of a known polymer to determine the relatedness of the polymer being analyzed to the known polymer. Comparison of signals is discussed in more detail below.

More than one detectable signal may be detected. For instance a first individual unit specific marker may interact with the agent or station to produce a first detectable signal and a second individual unit specific marker may interact with the agent or station to produce a second detectable signal different from the first detectable signal. This enables more than one type of unit specific marker to be detected on a single polymer.

Once the signal is generated it can then be detected. The particular type of detection means will depend on the type of signal generated which of course will depend on the type of interaction which occurs between the unit specific marker and the agent. Many interactions involved in the method of the invention will produce an electromagnetic radiation signal. Many methods are known in the art for detecting electromagnetic radiation signals, including two- and three-dimensional imaging systems. These and other systems are described in more detail in co-pending PCT Patent Application PCT/US98/03024 and U.S. Ser. No. 09/134,411.

Other interactions involved in the method will produce a nuclear radiation signal. As a radiolabel on a polymer passes through the defined region of detection, such as the station, nuclear radiation is emitted, some of which will pass through the defined region of radiation detection. A detector of nuclear radiation is placed in proximity of the defined region of radiation detection to capture emitted radiation signals. Many methods of measuring nuclear radiation are known in the art including cloud and bubble chamber devices, constant current ion chambers, pulse counters, gas counters (i.e., Geiger-Müller counters), solid state detectors (surface barrier detectors, lithium-drifted detectors, intrinsic germanium detectors), scintillation counters, Cerenkov detectors, etc.

Other types of signals generated are well known in the art and have many detections means which are known to those of skill in the art. Among these include opposing electrodes, magnetic resonance, and piezoelectric scanning tips. Opposing nanoelectrodes can function by measurement of capacitance changes. Two opposing electrodes create all area of energy storage, which is effectively between the two electrodes. It is known that the capacitance of two opposing electrodes change when different materials are placed between the electrodes. This value is known as a dielectric constant. Changes in the dielectric constant can be measured as a change in the voltage across the two electrodes. In the present example, different nucleotide bases or unit specific markers of a polymer may give rise to different dielectric constants. The capacitance changes as the dielectric constant of the unit specific marker of the polymer per the equation: $C=KC_o$, where K is the dielectric constant and $C_o$ is the capacitance in the absence of any bases. The voltage deflection of the nanoelectrodes is then outputted to a measuring device, recording changes in the signal with time.

A nanosized NMR detection device can be constructed to detect the passage of specific spin-labeled polymer unit specific markers. The nanosized NMR detection device consists of magnets which can be swept and a means of irradiating the polymer with electromagnetic energy of a constant frequency (This is identical to holding the magnetic field constant while the electromagnetic frequency is swept). When the magnetic field reaches the correct strength, the nuclei absorb energy and resonance occurs. This absorption causes a tiny electric current to flow in an antenna coil surrounding the sample. The signal is amplified and output to a recording device. For known labeled compounds, the time of detection is much faster than current means of NMR detection where a full spectra of the compound in question is required. Known labeled unit specific markers of polymers have known chemical shifts in particular regions, thereby eliminating the need to perform full spectral sweeps, lowering the time of detection per base to micro or milliseconds.

A nanoscale piezoelectric scanning tip can be used to read the different unit specific markers of the polymer based on physical contact of the different polymer unit specific markers with the tip. Depending on the size and shape of the polymer unit specific marker, different piezoelectric signals are generated, creating a series of unit specific marker dependent changes. Labels on unit specific markers are physically different than native units and can create a ready means for detection via a piezoelectric scanning tip. Upon contact of a polymer unit specific marker with the tip, the piezoelectric crystals change and give rise to a current which is outputted to a detection device. The amplitude and duration of the current created by the interaction of the polymer unit specific marker and the tip is characteristic of the polymer unit specific marker.

In one preferred type of linear analysis, the labeled polymer is fixed in a relative position to a station by a nanochannel, such that as the labeled polymer passes the station signals arising from the interaction between the station and the labeled polymer are spacially confined. The channels preferably correspond to the diameter of the labeled polymer and fix the DNA relative to an imaging system which is able to capture many emissions from the labeled polymer over an integrated period of time. The method is specific for the analysis of intensities of individual molecules. The nanochannel system is provided as an example and is discussed in more detail below. Any means can be used to fix the labeled polymers in a dimension for analysis by an optical method capable of analyzing the signals over time. Examples of devices which are capable of positioning labeled polymers for analysis include nanochannel arrays, integrated nanofabricated waveguides, and various lattices.

The methods of the invention are described herewith reference to several examples using polymers which are fluorescently labeled and which arc analyzed using a nanochannel device to simplify the discussion. The invention, however, is not limited to these examples and the other embodiments will be described more fully herein. In the example, fluorescently labeled polymers are drawn through a series of nanochannels. The planar surface of the nanochannels is illuminated via epiillumination. As the polymers cross the nanochannels, they are fixed in position relative to the imaging device, allowing for integration of the polymers fluorescence over time. The corresponding brightness of the fluorescence spots is indicative of the approximate length of the labeled polymers. The rationale behind the use of the restrictive structures is to fix the molecules relative to the detection system so that photon collection can occur in a fixed spatial dimension over time. In the embodiments when intensity is not being measured there is no need to fix the polymer relative to the imaging device. The time period that the polymer is fixed may be very short, and is just enough to make an intensity measurement.

As mentioned above, the signals arising from the polymers provide structural information about the polymer. The types of structural information that can be obtained are dependent on how the polymer is labeled and includes, for instance, all of the information described above as "unit specific information." The presence or absence of a particular sequence can be established by determining whether any polymers within the sample express a characteristic pattern of individual units which is only found in the polymer of interest i.e., by comparing the detected signals to a known pattern of signals characteristic of a known polymer to determine the relatedness of the polymer being analyzed to the known polymer. The entire sequence of the polymer of interest does not need to be determined in order to establish the presence or absence of the polymer in the sample. Similarly the methods may be useful for comparing the signals detected from one polymer to a pattern of signals from another polymer to determine the relatedness of the two polymers.

In one example the structural information provides the length of the polymer. The lengths of polymers are most easily determined from labeling all of the units of the polymer. As the polymers migrate past their respective restrictive nanostructures in a linear fashion, the photon flux from each of the restricted polymers is determined. An example using a nucleic acid is illustrated in FIGS. 1–11 wherein the nucleic acid is drawn through small channels in a membrane in a linear fashion by electrophoresis. The nucleic acid is labeled throughout the strand. The nucleic acid is excited by fluorescence epiillumination. The blackened membrane does not permit excitation of molecules below the membrane. As the fluorescently labeled nucleic acid molecules migrate past the nonochannels, they are fixed spatially. Integration of the collected signal gives rise to discrete, spatially separated intensity spots on the fluorescence image. The intensity of the spots are directly proportional to the length of the nucleic acid molecules. After electrophoretic migration past the channels, the nucleic acid is drawn out of the imaging area by a displaced electrode. Experimental details are provided in the Examples below.

The determination of the length of the polymer can be performed on a single polymer if each unit of the polymer is labeled. If most of the units of a plurality or polymers in a sample are labeled on each unit and the method is performed on a plurality of identical polymers then by comparing the intensities of the entire population the length can be determined.

In another example the structural information provides the number of polymers passing through a restrictive nanostructure in a given amount of time. The number of polymers can be determined by labeling each polymer with a fixed number of fluorophores. This can be accomplished for example by phosphate end-labeling the polymers using kits available from Molecular Probes. The brightness of the intensity spots in the analysis should be in fixed increments of two labels. A restrictive nanostructure with four polymers passing through it in a time (t) would give rise to an intensity spot of eight fluorophores.

In yet another example the structural information provides unit specific information about the polymer. In an example ssDNA are labeled with peptide nucleic acids (PNAs) which bind with high $T_m$ to the desired and specific sequences. The PNAs are cross-linked to the single-stranded DNA through uv crosslinking and the formation of PNA-DNA covalent complexes. The labeled PNAs are detected in the restrictive nanostructures. Based on the brightness of the individual wavelengths corresponding to the different probes used, information about the composition of internal sequences of a strand in question can be determined.

Figure 12B:
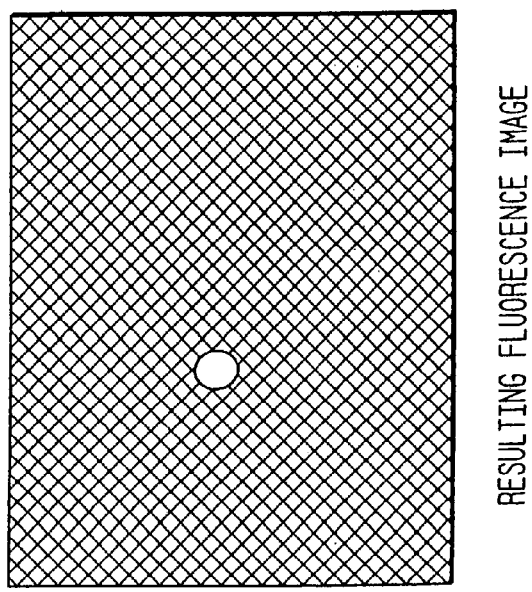
FIG. 12A is a schematic diagram of a waveguide structure with a labeled DNA molecule passing through it and 12B is similar to 11B.
Figure 12A:
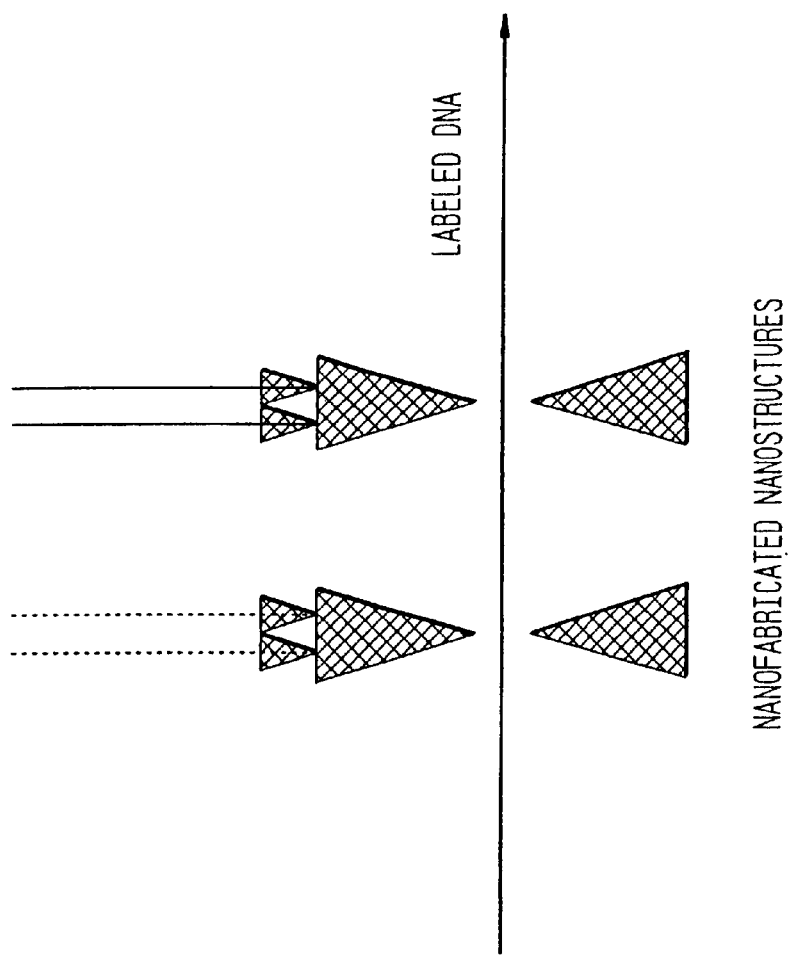

An example of a restrictive structure which enables measurement of intensity signals at a fixed station is a nanostructure fabricated by e-beam lithography and reactive ion etching as shown in FIG. 12. High resolution e-beam lithography is capable of fabricating structures with gap sizes on the order to 10 nm. These small structures can be used to restrict the movement of DNA. The structure shown in FIG. 12 is nanofabricated from quartz by e-beam lithography and reactive ion etching. Preferably it is a waveguide with a metallic surface. Multicolor excitation at each of the waveguides is initiated to excite the individual DNA molecules. The surfaces of the substrate are cleaned by an oxygen plasma cleaner. The hydrophillic surfaces are wetted and the top of the structures are sealed with a coverslip spin coated with silicone (Newark Electronics, NJ). The DNA molecules are migrated through the structures electrophoretically. Intensity images of the molecules are obtained. The total photon count per molecule is proportional to the length of the molecule.

Figure 13:
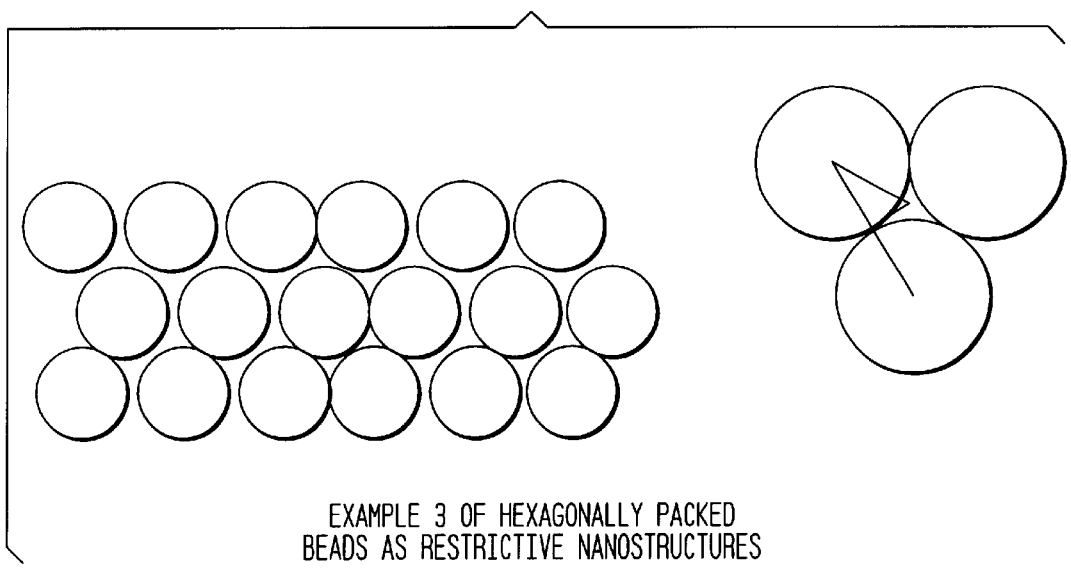
FIG. 13 is a schematic diagram of a hexagonally packed bead nanostructure for analyzing polymers.

Another example of a restrictive nanostructure which may be used is a monolayer of hexagonally packed beads which has the configuration shown in FIG. 13. The dimensions of the geometric areas between the beads can be easily calculated.

The methods of the invention can be used to identify one, some, or many of the units of the polymer. This is achieved by identifying the type of individual unit and its position on the backbone of the polymer by determining the intensity of a signal arising from the labeled polymer using labeled sequence specific probes as described in greater detail above.

In general the methods of linear polymer analysis using intensity are performed by detecting optical signals. An "optical signal" as used herein differs from a polymer dependent impulse and is a detectable electromagnetic radiation signal which transmits or conveys information about the structural characteristics of a polymer and from which a quantitative analysis of intensity can be determined. The optical signal may arise from energy transfer, quenching, radioactivity, or any other physical changes from which a quantitative measure of intensity can be derived. The signal preferably is optically detected. An "optically detectable" signal as used herein is a light based signal in the form of electromagnetic radiation which can be detected by light detecting imaging systems.

Optical detectable signals are generated, detected and stored in a database the signals can be analyzed to determine structural information about the polymer. The signals can be analyzed by assessing the intensity of the signal to determine structural information about the polymer. The computer may be the same computer used to collect data about the polymers, or may be a separate computer dedicated to data analysis. A suitable computer system to implement the present invention typically includes an output device which displays information to a user, a main unit connected to the output device and an input device which receives input from a user. The main unit generally includes a processor connected to a memory system via an interconnection mechanism. The input device and output device also are connected to the processor and memory system via the interconnection mechanism. Computer programs for data analysis of the detected signals are readily available from CCD manufacturers.

The methods of the invention can be accomplished using any device which produces a specific detectable polymer dependent impulse for an individual unit specific marker of a polymer. One type of device which enables this type of analysis is one which promotes linear transfer of a polymer past an interaction station or a signal generation station, such as, an article of manufacture including a wall material having a surface defining a channel, an agent selected from the group consisting of an electromagnetic radiation source, a quenching source, a luminescent film layer, and a fluorescence excitation source, attached to the wall material adjacent to the channel. Preferably the agent is close enough to the channel and is present in an amount sufficient to detectably interact with a partner compound selected from the group consisting of a light emissive compound and a quencher passing through the channel.

A wall material is a solid or semi-solid barrier of any dimensions which is capable of supporting at least one channel. A semi-solid material is a self supporting material and may be for instance a gel material such as a polyacrylamide gel. For instance the wall material may be composed of a single support material which may be conducting or non-conducting, light permeable or light impermeable, clear or unclear. In some instances the agent is embedded within the wall material. In these instances the wall material can be solely or partially made of a non-conducting layer, a light permeable layer or a clear layer to allow the agent to be exposed to the channel formed in the wall material to allow signal generation. When the wall material is only partially made from these materials the remaining wall material may be made from a conducting, light impermeable or unclear layer, which prevent signal generation. In some cases the wall material is made up of layers of different materials. For instance, the wall material may be made of a single conducting layer and a single non-conducting layer. Alternatively the wall material may be made of a single non-conducting layer surrounded by two conducing layers. Multiple layers and various combinations of materials are encompassed by the wall material of the invention.

As used herein a "luminescent film layer" is a film which is naturally luminescent or made luminescent by some means of excitation or illumination, e.g., electrooptic thin films and high index films illuminated by internal reflection.

As used herein a "material shield" is any material which prevents or limits energy transfer or quenching. Such materials include but are not limited to conductive materials, high index materials, and light impermeable materials. In a preferred embodiment the material shield is a conductive material shield. As used herein a "conductive material shield" is a material which is at least conductive enough to prevent energy transfer between donor and acceptor sources.

A "conductive material" as used herein is a material which is at least conductive enough to prevent energy transfer between a donor and an acceptor.

A "nonconductive material" as used herein is a material which conducts less than that amount that would allow energy transfer between a donor and an acceptor.

A "light permeable material" as used herein is a material which is permeable to light of a wavelength produced by the specific electromagnetic radiation, quenching source, or the fluorescence excitation source being used.

A "light impermeable material" as used herein is a material which is impermeable to light of a wavelength produced by the specific electromagnetic radiation, quenching source, or the fluorescence excitation source being used.

A "channel" as used herein is a passageway through a medium through which a polymer can pass. The channel can have any dimensions as long as a polymer is capable of passing through it. For instance the channel may be an unbranched straight cylindrical channel or it may be a branched network of interconnected winding channels. Preferably the channel is a straight nanochannel or a microchannel. A "nanochannel" as used herein is a channel having dimensions on the order of nanometers. The average diameter of a nanochannel is between 1 nm and 999 nm. A "microchannel" as used herein is a channel having dimensions on the order of micrometers. The average diameter of a microchannel is between 1 $\mu$m and 1 mm. Preferred specifications and dimensions of channels useful according to the invention are set forth in detail below. In a preferred embodiment, the channel is fixed in the wall.

An agent is attached to the wall material in such a manner that it will detectably interact with a partner compound by undergoing energy transfer or quenching with the partner light emissive compound which is passing through the channel of the wall material. In order to interact with the partner compound the agent can be positioned in close proximity to the channel. For example, the agent may be attached to the inside of the channel, attached to the external surface of the wall material, attached to a concentrated region of the external surface of the wall material surrounding the rim of the channel, embedded within the wall material, or embedded in the form of a concentric ring in the wall material surrounding the channel. Optionally the agent may cover the entire surface of the wall material or may be embedded throughout the entire wall material. In order to improve signal generation when the agent is not localized, a mask may be used to cover some areas of the wall material such that only localized regions of agent are exposed. A "mask" as used herein is an object which has openings of any size or shape. More than one agent may be attached to the wall material in order to produce different signals when the agents are exposed to the partner agent.

The agent may be attached to the surface of the wall material by any means of performing attachment known in the art. Examples of methods for conjugating biomaterials are presented in Hermanson, G. T., *Bioconjugate Techniques,* Academic Press, Inc., San Diego, 1996, which is hereby incorporated by reference.

When the agent is attached to the surface of the wall material it may be attached directly to the wall material or it may be attached via a linker. A "linker" as used herein with respect to the attachment of the agent is a molecule that tethers a light emitting compound or a quenching compound to the wall material. Linkers are well known in the art. Commonly used linkers include alkanes of various lengths.

The agent is attached to the wall material in an amount sufficient to detectably interact with a partner light emissive compound. As used herein a "partner light emissive compound" is a light emissive compound as defined above but which specifically interacts with and undergoes energy transfer or quenching when positioned in close proximity to the agent. The amount of partner light emissive compound and the amount of agent required will depend on the type of agent and light emissive compound used.

Another example of an article of manufacture which is useful for practicing the method of the invention is a wall material having a surface defining a plurality of channels and a station attached to a discrete region of the wall material adjacent to at least one of the channels, wherein the station is close enough to the channel and is present in an amount sufficient to cause a signal to arise from a detectable physical change in a polymer of linked unit specific markers passing through the channel or in the station as the polymer is exposed to the station. A "discrete region" of the wall material adjacent to at least one of the channels is a local area which is surrounded by wall material not having a station. The area surrounding the discrete region does not interact with the unit specific marker to produce the same characteristic signal produced by the interaction of the unit specific marker with the station. The discrete region is positioned in or near the channel such that the station at the discreet region is exposed to the unit specific marker as it traverses the channel.

An additional article of manufacture useful for practicing the method of the invention is a wall material having a surface defining a channel and a plurality of stations each attached to a discrete region of the wall material adjacent to the channel, wherein the stations are close enough to the channel and are present in an amount sufficient to cause a signal to arise from a detectable physical change in a polymer of linked unit specific markers passing through the channel or in the station as the polymer is exposed to the station.

As used herein a "plurality of stations" is at least two stations. Preferably a plurality of stations is at least three stations. In another preferred embodiment a plurality of stations is at least five stations.

PCT Patent Application PCT/US98/03024 provides a detailed description of an optimal design of a nanochannel plate having fluorophores embedded within the plate as well as other articles useful for practicing the methods of the invention. The methods of the invention are not limited, however, to the use of articles of manufacture described herein or in the priority PCT application. The examples are provided for illustrative purposes only. The methods of the invention can be performed using any system in which a plurality of unit specific markers of a polymer can be moved with respect to a fixed station and from which signals can be obtained.

A preferred method of the invention involves the analysis of radiolabeled polymers as discussed above. Preparation of radiolabeled polymers such as DNA (for example, with $^{32}P$ or $^{3}H$) is known in the art. The following description represents one of the many possible embodiments of analyzing radiolabeled polymers according to the methods of the invention. A radiolabeled nucleic acid molecule is analyzed with a single fabricated multilayered nanochannel. The nanochannel is the diameter of the labeled nucleic acid molecule and is constructed to yield a defined region of detection. Exemplary nanochannel plates include a heterogeneous multilayered structure consisting of two radiation impermeable layers such as lead or Lucite films and a film of lower density material (or scintillation layer) (i.e., conventional polymers, polymethylmethacrylate, polystyrene, Teflon, etc.). The lead films sandwich the layer of lower density material and are of such thickness as to prevent passage of radiation. The lower density material permits passage of radiation, thereby creating a defined region of radiation detection. As the radiolabel on the DNA passes through the defined region of detection, nuclear radiation is emitted, some of which will pass through the defined region of radiation detection.

In a related embodiment of analysis of radiolabeled nucleotides a detection system based on scintillation counting and multiple nanochannels is presented. A nanochannel array is fabricated. Multiple multilayered channels exist for parallel amplification of data output. Each individual channel consists of two nuclear radiation shielding layers which shield nuclear radiation, and a scintillation layer which is fluorescently excited with exposure to nuclear radiation. The individual channels are separated from each other by a nuclear radiation shielding material. The nuclear radiation is prevented from reaching the fluorescent detection system by overlaying with optical quality Lucite (or any other transparent material which prevents the passage of nuclear radiation). This allows only the fluorescent signal to reach the detection system.

Each of the above described nanochannels is only an example. It is, therefore, anticipated that each of the limitations described with respect to these embodiments involving any one element or combinations of elements can be included in each nanochannel. Preparation of films having multiple layers of differing material have been described in the art, e.g., U.S. Pat. No. 5,462,467, Ferreira et. al., *Thin Solid Films* 244:806–809 (1994).

In one embodiment the signal station is fixed. A station is "fixed" as used herein if the station and the detection device do not move. The polymer may move past the fixed station but the station does not move. In one embodiment the station is an interaction station. As used herein an "interaction station or site" is a region where a unit specific marker of the polymer interacts with an agent and is positioned with respect to the agent in close enough proximity whereby they can interact. The interaction station for fluorophores, for example, is that region where they are close enough so that they energetically interact to produce a signal.

Methods for preparing the wall material and the various light conductive and non-conductive layers etc are described in co-pending PCT Patent Application PCT/US98/03024.

An example of an apparatus constructed to hold a nanochannel (or microchannel) plate which is capable of generating an electric field is described The electric field, created by electrodes, is used to draw the DNA through the nanochannels. The exemplary nanochannel plate is immersed in a slightly viscous buffer solution which helps to slow the transit of the polymer through the nanochannel, so as to allow for a longer signal collection time per base. In addition, on either side of the plate are electrodes immersed in the buffer solution. The ensemble of nanochannel plate, buffer compartments, and electrodes are contained in an optical quality glass chamber suitable for image analysis and are positioned adjacent to a 60×1.4 NA oil objective.

As discussed above the use of an electric field to cause the polymer to move linearly through a channel is preferred. The use of an electric field is suitable because the stretched, linear orientation of a polymer in an electric field is favorable for linear crossing of nanochannels. Furthermore, the rate of polymer movement can be controlled by voltage. Lastly, an electric field does not adversely affect FRET.

Light microscopy (Bustamante, 1991; Gurrieri et al., 1990; Matsumoto et al., 1981, Rampino and Chrambach, 1990; Schwartz and Koval, 1989; Smith et al., 1989), linear dichroism (LD) (Åkerman et al., 1990; Åkerman et al., 1985, Moore et al., 1986), fluorescence-detected LD (Holzwarth et al., 1987), and linear birefringence (Sturm and Weill, 1989; Chu et al., 1990) can be used to study the instantaneous changes in shape of DNA molecules undergoing gel electrophoresis. In these studies DNA is shown to be strongly oriented and stretched.

Gurrieri et al., 1990 has demonstrated linear and stretched conformation of DNA molecules in an electric field. In each of the cases, the DNA molecule is clearly aligned in the direction of the applied electric field. The method used to visualize the DNA molecules combines fluorescent DNA labeling and use of an image intensifier-video camera system (Bustamante, 1991; Houseal et al., 1989; Morikawa and Yanagida, 1981; Matsumoto et al., 1989; Yanagida et al., 1983). The DNA molecules shown are T2 molecules which are 164 kbp long.

The orientation of DNA in an electric field has been well studied with linear dichroism and electric dichroism (Ding et al., 1972; Yamaoka and Charney 1973; Colson et al., 1974; Hogan et al., 1978; Priore and Allen, 1979; Yamaoka and Matsuda, 1981; Wu et al., 1981). In fact, the first studies done on DNA orientation have been performed with these two techniques. DNA was first studied in solution and then subsequently in electrophoretic gels. Studies both in solution and in gels yield similar results in that the DNA molecules are indeed oriented in the direction of the electric field.

The invention in another aspect is a kit for labeling polymers. The kit includes a container housing a series of distinct nucleic acid probes; wherein the series of nucleic acid probes is a set of multiple base pair probes. Preferably the multiple base pair probes are selected from the group consisting of two base pair probes, three base pair probes, four base pair probes, and five base pair probes, but may be any number of base pairs greater than one.

A "base pair probe" as used herein refers to a single stranded nucleic acid fragment that call be used to hybridize to an unknown sequence. The term is used consistently with it's common meaning in the art. A "set of multiple base pair probes" as used herein is a series of base pair probes of a specific length, wherein the series of probes includes each possible combination of nucleic acid sequences of that particular length. For any given number of nucleic acid sequences, the number of different base pair probes which can be used is defined by the formula $4^n$, where n is the number of nucleic acid sequences. For instance a two base pair probe, which spans two nucleotides, would include 16 combinations of nucleotide pairs. These include, AC, AG, AT, AA, CC, CA, CG, CT, GA, GG, GC, GT, TA, TC, TG, and TT. A three base pair probe, which spans three nucleotides, would include a combination of 54 three nucleotide pairs combinations. Those of ordinary skill in the art would easily be able to identify each of the different combinations.

In one embodiment the container is a single container having a plurality of compartments, each housing a specific labeled probe. In another embodiment the container is it plurality of containers. An example of a kit is presented in FIG. 10.

The kit in one embodiment also includes instructions for labeling the nucleic acid probes, if the probes are not already labeled.

The distinct nucleic acid probes are labeled in one embodiment. Preferably the nucleic acid probes are labeled with an agent selected from the group consisting of an electromagnetic radiation source, a quenching source and a fluorescence excitation source. In one embodiment the plurality of polymers is a homogeneous population. In another embodiment the distinct nucleic acid probes are three base pair probes. In another embodiment the distinct nucleic acid probes are four base pair probes. In yet another embodiment the distinct nucleic acid probes are five base pair probes.

EXAMPLES

Example 1

The DNA solution is prepared by mixing together with TOTO-1 obtained from Molecular Probes, OR. TOTO-1 is a dimeric cyanine dye which is virtually nonfluorescent in the absence of binding to dsDNA. Upon binding the fluorescence is increased over 1000-fold. Excitation of the dye is at 514 nm and emission is at 533. Nanomolar concentrations of the dye is used in 0.5×TBE buffer. The polycarbonate membrane are blackened by dissolving 2 gm of Irgalan black (Chemical Index, acid black 107) in 1 L of 2% acetic acid. Membranes are soaked in Irgalan black solution for 24 hours. The samples are rinsed with water and dried in air. The membrane is mounted in a dual buffer compartment which has an optical window for collecting fluorescence images. An electric field between 1 V/cm to 20 V/cm is used to electrophoretically drive the DNA through the nanochannels which can range in diameter of 5 nm to 10 nm. DNA crossing the nanochannels non-linearly would give aberrant intensity signals which, upon statistical average, would give rise to noise.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

I claim:

1. A method for determining an order of at least two labeled unit specific markers of a polymer comprising, obtaining polymer dependent impulses for at least two labeled unit specific markers of a plurality of polymers, wherein at least one of the two labeled unit specific markers labels an internal unit, comparing the polymer dependent impulses obtained from each of the plurality of polymers, wherein fewer than all of the polymer dependent impulses that could arise from labeling of the polymer are detected, determining an order of the at least two labeled unit specific markers from the polymers based upon comparing the polymer dependent impulses.

2. The method of claim 1, wherein the plurality of polymers is a homogenous population.

3. The method of claim 1, wherein fewer than all of the polymer dependent impulses arising from unit specific markers are detected.

4. The method of claim 1, wherein the polymers are randomly labeled.

5. The method of claim 3, wherein the polymer dependent impulses arise from at least two unit specific markers of the polymers.

6. The method of claim 1, wherein the polymer is a nucleic acid.

7. The method of claim 6, wherein the obtained polymer dependent impulses includes the time of separation between unit specific markers.

8. The method of claim 6, wherein the unit specific markers are nucleic acid probes.

9. The method of claim 8, wherein the unit specific markers are two base pair nucleic acid probes.

10. The method of claim 8 wherein the unit specific markers are three base pair nucleic acid probes.

11. The method of claim 6, wherein the unit specific markers are peptide nucleic acid probes.

12. The method of claim 6, wherein the obtained polymer dependent impulses indicate the sequence of units of the polymer.

13. The method of claim 1, wherein a portion of the unit specific markers are unknown.

14. The method of claim 1, wherein the analysis of each polymer is spatially separate.

15. A method for sequencing a polymer of linked units comprising, obtaining polymer dependent impulses from a plurality of overlapping polymers, at least a portion of each of the polymers having a sequence of linked units identical to the other of the polymers, wherein the plurality of polymers is randomly labeled and comparing the polymer dependent impulses from an overlapping portion of each of the plurality of polymers to obtain a sequence of linked units which is identical in the plurality of polymers.

16. The method of claim 15, wherein the polymer dependent impulses are optically detectable.

17. The method of claim 15, wherein the plurality of polymers is a homogeneous population.

18. The method of claim 15, wherein the plurality of polymers is a heterogeneous population.

19. The method of claim 15, wherein the polymers are nucleic acids.

20. The method of claim 19, wherein the nucleic acids are labeled with an agent selected from the group consisting of an electromagnetic radiation source, a quenching source and a fluorescence excitation source.

21. The method of claim 15, wherein each polymer is analyzed separately.

22. A method for analyzing a polymer, comprising linearly moving a labeled polymer with respect to a fixed station, obtaining a signal from the labeled polymer as the labeled polymer passes the fixed station, wherein the signal is an electromagnetic radiation signal arising from an interaction between at least two distinct labeled unit specific markers and the fixed station, and determining a quantitative measure of intensity of the signal to analyze the polymer.

23. The method of claim 22, wherein each unit of the labeled polymer is labeled and the quantitative measure of intensity of the signal indicates the length of the polymer.

24. The method of claim 22, wherein less than all units of the polymer are labeled with at least one unit specific marker and the quantitative measure of intensity of the signal indicates the number of labeled unit specific markers present in the polymer.

25. The method of claim 22, wherein the fixed station is an electromagnetic radiation source.

26. The method of claim 22, wherein the fixed station is a radiation source.

27. The method of claim 22, wherein a plurality of polymers are analyzed simultaneously to produce a plurality of signals, one signal for each polymer, and further comprising the step of comparing the intensities of the signals to analyze the polymers.

28. The method of claim 22, wherein a plurality of polymers are analyzed simultaneously to produce a signal.

29. The method of claim 28, wherein the number of polymers is known and wherein each of the polymers is identically labeled and further comprising the step of dividing the quantitative measure of intensity by the number of polymers to determine the number of labeled unit specific markers in each polymer.

30. The method of claim 22, wherein the units are labeled with a peptide nucleic acid probe.

31. The method of claim 22, wherein the units are labeled with a series of distinct nucleic acid probes selected from the group consisting of two base pair probes, three base pair probes, four base pair probes, and five base pair probes.

32. The method of claim 22, wherein the units are labeled with a fluorescent probe.

33. The method of claim 22, wherein the labeled polymer is labeled with a plurality of unit specific markers, wherein at least one unit specific marker includes a fluorophore which emits light at a first wavelength and at least one unit specific marker which includes a fluorophore which emits light at a second wavelength.

34. The method of claim 33 wherein the at least one unit specific marker which includes the fluorophore which emits light at the first wavelength is attached to end units of the polymer and wherein the at least one unit specific marker which includes the fluorophore which emits light at the second wavelength is attached to an internal unit of the polymer.

35. A method for sequencing a polymer of linked units comprising, analyzing a polymer by obtaining polymer dependent impulses from a plurality of overlapping polymers, at least a portion of each of the polymers having a sequence of linked units identical to the other of the polymers, wherein the analysis of the plurality of polymers is performed simultaneously and comparing the polymer dependent impulses from an overlapping portion of each of the plurality of polymers to obtain a sequence of linked units which is identical in the plurality of polymers.

* * * * *

UNITED STATES PATENT AND TRADEMARK OFFICE
CERTIFICATE OF CORRECTION

PATENT NO. : 6,403,311 B1
DATED : June 11, 2002
INVENTOR(S) : Eugene Y. Chan

It is certified that error appears in the above-identified patent and that said Letters Patent is hereby corrected as shown below:

<u>Title page,</u>
Line [60], Related U.S. Application Data, delete the following:

"Provisional application No. 60/096,666, filed on Aug. 13, 1998, provisional application No. 60/120,662, filed on Aug. 13, 1998, provisional application No. 60/096,687, filed on May 5, 1997, and provisional application No. 60/037,921 filed February 12, 1997."

and insert the following:

-- Provisional application No. 60/096,666, filed on Aug. 13, 1998, provisional application No. 60/096,662, filed in Aug. 13, 1998, provisional application No. 60/064,687, filed on November 5, 1997, and provisional application No. 60/037,921 filed February 12, 1997. --

Signed and Sealed this

Eighth Day of July, 2003

JAMES E. ROGAN
*Director of the United States Patent and Trademark Office*

SEQUENCE LISTING

```
<160> NUMBER OF SEQ ID NOS: 3

<210> SEQ ID NO 1
<211> LENGTH: 9
<212> TYPE: DNA
<213> ORGANISM: Artificial Sequence
<220> FEATURE:
<223> OTHER INFORMATION: Synthetic sequence

<400> SEQUENCE: 1 aggcaaacg                                                              9

<210> SEQ ID NO 2
<211> LENGTH: 10
<212> TYPE: DNA
<213> ORGANISM: Artificial Sequence
<220> FEATURE:
<223> OTHER INFORMATION: Synthetic sequence
```

-continued

```
<400> SEQUENCE: 2
agtgcaaacg                                                                10

<210> SEQ ID NO 3
<211> LENGTH: 16
<212> TYPE: DNA
<213> ORGANISM: Artificial Sequence
<220> FEATURE:
<223> OTHER INFORMATION: Synthetic sequence

<400> SEQUENCE: 3
acgtacgtac gtacgt                                                         16
```